(12) United States Patent
Sutariya et al.

(10) Patent No.: US 11,471,412 B1
(45) Date of Patent: Oct. 18, 2022

(54) NANOPARTICLES AND NANOGEL DRUG COMPOSITIONS FOR TREATMENT OF AGE-RELATED MACULAR DEGENERATION

(71) Applicant: University of South Florida, Tampa, FL (US)

(72) Inventors: Vijaykumar Bhadabhai Sutariya, Tampa, FL (US); Priyanka Sureshbhai Bhatt, Tampa, FL (US); Vipul B. Amin, Iselin, NJ (US); Srinivas M. Tipparaju, Tampa, FL (US)

(73) Assignee: University of South Florida, Tampa, FL (US)

( * ) Notice: Subject to any disclaimer, the term of this patent is extended or adjusted under 35 U.S.C. 154(b) by 151 days.

(21) Appl. No.: 16/870,446

(22) Filed: May 8, 2020

Related U.S. Application Data

(60) Provisional application No. 62/846,453, filed on May 10, 2019.

(51) Int. Cl.
| | | |
|---|---|---|
| A61K 9/14 | (2006.01) | |
| A61K 9/06 | (2006.01) | |
| A61K 47/34 | (2017.01) | |
| A61K 31/404 | (2006.01) | |

(52) U.S. Cl.
CPC .......... *A61K 9/14* (2013.01); *A61K 9/06* (2013.01); *A61K 31/404* (2013.01); *A61K 47/34* (2013.01)

(58) Field of Classification Search
CPC .... A61K 9/5153; A61K 31/506; A61K 31/24; A61K 31/366; A61K 31/4412; A61K 9/14
See application file for complete search history.

(56) References Cited

U.S. PATENT DOCUMENTS

| | | | |
|---|---|---|---|
| 7,727,554 B2 | 6/2010 | Labhasetwar et al. | |
| 2017/0273901 A1* | 9/2017 | Fu ...................... | A61K 31/404 |

FOREIGN PATENT DOCUMENTS

| | | |
|---|---|---|
| WO | 1995003357 | 2/1995 |
| WO | 2013127949 | 9/2013 |
| WO | 2016100392 | 6/2016 |

OTHER PUBLICATIONS

Alshetaili et al (Tropical Journal of Pharmaceutical Research, Jul. 2018, vol. 17, pp. 1263-1269) (Year: 2018).*
Murphy et al (Mol Cancer Ther, 2011, vol. 10, pp. 972-982) (Year: 2011).*
Hirani et al (Pharmaceutical Development and Technology, 2016, vol. 21, pp. 61-67) (Year: 2016).*
Danafar (Cogent Medicine, 2016, vol. 3, pp. 1-11) (Year: 2016).*
Al Gwairi O, Thach L, Zheng W, Osman N, Little PJ. Cellular and molecular pathology of age-related macular degeneration: potential role for proteoglycans. Journal of ophthalmology. 2016;2016.
Alshetaili AS, Anwer MK, Alshahrani SM, Alalaiwe A, Alsulays BB, Ansari MJ, et al. Characteristics and anticancer properties of Sunitinib malate-loaded poly-lactic-co-glycolic acid nanoparticles against human colon cancer HT-29 cells lines. 2018;17(7):1263-9.
Al-Zamil WM, Yassin SA. Recent developments in age-related macular degeneration: a review. Clinical interventions in aging. 2017;12:1313-30.
Ambasta RK, Sharma A, Kumar PJVc. Nanoparticle mediated targeting of VEGFR and cancer stem cells for cancer therapy. 2011;3(1):26.
Bhatt P, Khatri N, Kumar M, Baradia D, Misra A. Microbeads mediated oral plasmid DNA delivery using polymethacrylate vectors: an effectual groundwork for colorectal cancer. Drug delivery. 2015;22(6):849-61.
Bhatt P, Lalani R, Mashru R, Misra A. Abstract 2065: Anti-FSHR antibody Fab' fragment conjugated immunoliposomes loaded with cyclodextrin-paclitaxel complex for improved in vitro efficacy on ovarian cancer cells. Cancer Research. 2016;76(14 Supplement):2065.
Bhatt P, Lalani R, Vhora I, Patil S, Amrutiya J, Misra A, et al. Liposomes encapsulating native and cyclodextrin enclosed paclitaxel: Enhanced loading efficiency and its pharmacokinetic evaluation. International Journal of Pharmaceutics. 2018;536(1):95-107.
Carmeliet PJO. VEGF as a key mediator of angiogenesis in cancer. 2005;69(Suppl. 3):4-10.
Chou R, Dana T, Bougatsos C, Grusing S, Blazina I. Screening for Impaired Visual Acuity in Older Adults: Updated Evidence Report and Systematic Review for the US Preventive Services Task Force. JAMA. 2016;315(9):915-33.
Clinical trial: NCT03249740 (First posted on Aug. 15, 2017 https://clinicaltrials.gov/ct2/show/NCT03249740.
Clinical trial: NCT03953079 (First posted on May 19, 2019) https://clinicaltrials.gov/ct2/show/NCT03953079.
Clinical trial: NCT04085341 (First posted on Sep. 21, 2019) https://clinicaltrials.gov/ct2/show/NCT04085341.
Cristina Maria de Barros, Sean Geary, Aliasger Salem, Department of Pharmaceutical Sciences and experimental Therapeutics, College of Pharmacy, University of Iowa, Sunitinib-Loaded Polymeric Nanoparticles to Deplete Myeloid-Derived Suppressor Cells and Enhance the Efficacy of a Cancer Immunotherapy, Presented at Pharmaceutical and Pharmacological Sciences Research Retreat on May 19, 2017.
Day S, Acquah K, Mruthyunjaya P, Grossman DS, Lee PP, Sloan FAJAjoo. Ocular complications after anti-vascular endothelial growth factor therapy in medicare patients with age-related macular degeneration. 2011;152(2):266-72.
Del Amo EM, Rimpelä A-K, Heikkinen E, Kari OK, Ramsay E, Lajunen T, et al. Pharmacokinetic aspects of retinal drug delivery. Progress in retinal eye research. 2017;57:134-85.
Espana-Serrano L, Chougule MB. Enhanced Anticancer Activity of PF-04691502, a Dual PI3K/mTOR Inhibitor, in Combination With VEGF siRNA Against Non-small-cell Lung Cancer. Molecular therapy Nucleic acids. 2016;5(11):e384.

(Continued)

*Primary Examiner* — Mark V Stevens
(74) *Attorney, Agent, or Firm* — Meunier Carlin & Curfman LLC

(57) ABSTRACT

Disclosed are nanoparticles and nanogel drug compositions and the use thereof for treating age-related macular degeneration.

14 Claims, 11 Drawing Sheets

(56) References Cited

OTHER PUBLICATIONS

Gaudana R, Jwala J, Boddu SH, Mitra AKJPr. Recent perspectives in ocular drug delivery. 2009;26(5):1197.

Goel PN, Gude RP. Unravelling the antimetastatic potential of pentoxifylline, a methylxanthine derivative in human MDA-MB-231 breast cancer cells. Molecular and cellular biochemistry. 2011;358(1-2):141-51.

Hirani A, Grover A, Lee YW, Pathak Y, Sutariya V. Triamcinolone acetonide nanoparticles incorporated in thermoreversible gels for age-related macular degeneration. Pharmaceutical development and technology. 2016;21(1):61-7.

Hoare TR, Kohane DS. Hydrogels in drug delivery: Progress and challenges. Polymer. 2008;49(8):1993-2007.

Hulkower KI, Herber RLJP. Cell migration and invasion assays as tools for drug discovery. 2011;3(1):107-24.

Huo M, Zhao Y, Satterlee AB, Wang Y, Xu Y, Huang LJJoCR. Tumor-targeted delivery of sunitinib base enhances vaccine therapy for advanced melanoma by remodeling the tumor microenvironment. 2017;245:81-94.

Jager RD, Mieler WF, Miller JW. Age-related macular degeneration. New England Journal of Medicine. 2008;358(24):2606-17.

Kathleen Halasz, Shannon JK, Iqbal MT, Yashwant P, Vijaykumar S. Utilization of Apatinib-Loaded Nanoparticles for the Treatment of Ocular Neovascularization. Current Drug Delivery. 2019;16(2):153-63.

Kim KL, Suh W. Apatinib, an Inhibitor of Vascular Endothelial Growth Factor Receptor 2, Suppresses Pathologic Ocular Neovascularization in Mice. Investigative ophthalmology & visual science. 2017;58(9):3592-9.

Kovach JL, Schwartz SG, Flynn HW, Scott IUJJoo. Anti-VEGF treatment strategies for wet AMD. 2012, 786870.

Le Tourneau C, Raymond E, Faivre S. Sunitinib: a novel tyrosine kinase inhibitor. A brief review of its therapeutic potential in the treatment of renal carcinoma and gastrointestinal stromal tumors (GIST). Therapeutics clinical risk management. 2007;3(2):341.

Makadia HK, Siegel SJ. Poly lactic-co-glycolic acid (PLGA) as biodegradable controlled drug delivery carrier. Polymers. 2011;3(3):1377-97.

Medina C, Santos-Martinez M, Radomski A, Corrigan O, Radomski MJBjop. Nanoparticles: pharmacological and toxicological significance. 2007;150(5):552-8.

Mena AC, Pulido EG, Guillen-Ponce C. Understanding the molecular-based mechanism of action of the tyrosine kinase inhibitor: sunitinib. Anti-cancer drugs. 2010;21:S3-S11.

Michels S, Rosenfeld PJ, Puliafito CA, Marcus EN, Venkatraman ASJO. Systemic bevacizumab (Avastin) therapy for neovascular age-related macular degeneration: twelve-week results of an uncontrolled open-label clinical study. 2005;112(6):1035-47. e9.

Murphy KM, Ouyang W, Farrar JD, Yang J, Ranganath S, Asnagli H, et al. Signaling and transcription in T helper development. Annual review of immunology. 2000;18(1):451-94.

Nickla DL, Wallman J. The multifunctional choroid. Progress in retinal eye research. 2010;29(2):144-68.

Nowak JZ. Age-related macular degeneration (AMD): pathogenesis and therapy. Pharmacological Reports. 2006;58(3):353.

Patel J, Amrutiya J, Bhatt P, Javia A, Jain M, Misra A. Targeted delivery of monoclonal antibody conjugated docetaxel loaded PLGA nanoparticles into EGFR overexpressed lung tumour cells. Journal of microencapsulation. 2018;35(2):204-17.

Patil S, Bhatt P, Lalani R, Amrutiya J, Vhora I, Kolte A, et al. Low molecular weight chitosan-protamine conjugate for siRNA delivery with enhanced stability and transfection efficiency. RSC Advances. 2016;6(112):110951-63.

Pennington KL, DeAngelis MM. Epidemiology of age-related macular degeneration (AMD): associations with cardiovascular disease phenotypes and lipid factors. Eye vision. 20163(1):34.

Pernis AB, Rothman PB. JAK-STAT signaling in asthma. The Journal of clinical investigation. 2002;109(10):1279.

Pirooznia N, Hasannia S, Lotfi AS, Ghanei M. Encapsulation of alpha-1 antitrypsin in PLGA nanoparticles: in vitro characterization as an effective aerosol formulation in pulmonary diseases. Journal of nanobiotechnology. 2012;10:20.

Pożarowska D, Pożarowski P. The era of anti-vascular endothelial growth factor (VEGF) drugs in ophthalmology, VEGF and anti-VEGF therapy. Central-European journal of immunology. 2016;41(3):311.

Priyanka Bhatt, Priya Narvekar, Yashwant Pathak, Vijaykumar Sutariya. Thermo-reversible gel formulation containing Sunitinib loaded PLGA nanoparticles for ocular delivery. AAPS PharmSci 360 annual meeting & exposition 2018, Nov. 4-7, 2018, at Walter E. Washington Convention Center, Washington, DC, USA.

Priyanka Bhatt, Yashwant Pathak, Vijaykumar Sutariya. Delivery of anti-VEGF agents for ocular neovascularization. Forth annual Vision Florida symposium, 2019, Jan. 24-25, 2019, at University of South Florida, Tampa, FL,USA. p. 18.

Sadat SM, Jahan ST, Haddadi AJJoB, Nanobiotechnology. Effects of size and surface charge of polymeric nanoparticles on in vitro and in vivo applications. 2016;7(02):91.

Saint-Geniez M, Maharaj AS, Walshe TE, Tucker BA, Sekiyama E, Kurihara T, et al. Endogenous VEGF is required for visual function: evidence for a survival role on Müller cells and photoreceptors. 2008;3(11):e3554.

Schwartz SG, Flynn Jr HW, Scott IUJEoop. Endophthalmitis after intravitreal injections. 2009;10(13):2119-26.

Schwartz SG, Scott IU, Flynn Jr HW, Stewart MW. Drug delivery techniques for treating age-related macular degeneration. Expert opinion on drug delivery. 2014;11(1):61-8.

Semete B, Booysen L, Lemmer Y, Kalombo L, Katata L, Verschoor J, et al. In vivo evaluation of the biodistribution and safety of PLGA nanoparticles as drug delivery systems. Nanomedicine: Nanotechnology, Biology Medicine. 2010;6(5):662-71.

Senger DR, Davis GE. Angiogenesis. Cold Spring Harbor perspectives in biology. 2011, 3(8):a005090-a.

Shahiwala A, Misra A. In-Vitro and In-Vivo Tools in Drug Delivery Research for Optimum Clinical Outcomes 2018.

Shang Q, Zhai J, Tian R, Zheng T, Zhang X, Liang X, et al. Fabrication, characterization, and controlled release of eprinomectin from injectable mesoporous PLGA microspheres. RSC Advances. 2015;5(92):75025-32.

Sharma S, Johnson D, Abouammoh M, Hollands S, Brissette AJCJoOJCdO. Rate of serious adverse effects in a series of bevacizumab and ranibizumab injections. 2012;47(3):275-9.

Singh R, Kesharwani P, Mehra NK, Singh S, Banerjee S, Jain NK. Development and characterization of folate anchored Saquinavir entrapped PLGA nanoparticles for anti-tumor activity. Drug development and industrial pharmacy. 2015;41(11):1888-901.

Stevenson CL, Santini Jr JT, Langer RJAddr. Reservoir-based drug delivery systems utilizing micro technology. 2012;64(14):1590-602.

Yashwant Pathak, Priyanka Bhatt, Vijaykumar Sutariya, Yashwant Pathak. Nanoparticulate Ophthalmic Drug Delivery Systems using Polymeric ThermoReversible Materials. NanoFlorida 2018 conference, Oct. 5-7, 2018, at Florida tech, Melbourne, FL, USA, p. 48.

Yewale C, Baradia D, Patil S, Bhatt P, Amrutiya J, Gandhi R, et al. Docetaxel loaded immunonanoparticles delivery in EGFR overexpressed breast carcinoma cells. Journal of Drug Delivery Science and Technology. 2018;45:334-45.

Zhang C, Qineng P, Zhang H. Self-assembly and characterization of paclitaxel-loaded N-octyl-O-sulfate chitosan micellar system. Colloids and surfaces B, Biointerfaces. 2004;39(1-2):69-75.

\* cited by examiner

NANOPARTICLES AND NANOGEL DRUG COMPOSITIONS FOR TREATMENT OF AGE-RELATED MACULAR DEGENERATION

CROSS REFERENCE TO RELATED APPLICATIONS

This application claims the benefit of priority to U.S. Provisional Patent Application No. 62/846,453, filed May 10, 2019, the disclosure of which is expressly incorporated herein by reference.

FIELD

The present disclosure relates to nanoparticles and nanogel drug compositions and uses thereof for treating age-related macular degeneration (AMD).

BACKGROUND

Age-related macular degeneration (AMD) is a leading cause of vision loss affecting geriatric/elderly patients in developed nations. AMD ranks third among the global causes of visual impairment with a blindness prevalence of 8.7%. There are million patients with advanced AMD and more than 8 million patients with an intermediate form of AMD. Of the two types of AMD, namely, exudative and non-exudative, the former is a leading cause of severe vision loss and is associated with neovascularization of choroid plexus. The blurring of vision occurs due to damage to macular region in retinal epithelium due to build-up of acellular debris at the site. As a follow up event to damage to epithelial layer, secretion of cytokines such as vascular endothelial growth factors (VEGF), ion channel dysfunction and abnormal lipid metabolism lead to oxidative damage of cells. To compensate for the decrease blood supply at retinal region, neovascularization occurs that may lead to increase in risk of fluid deposition, inflammation, vascular occlusion and hemorrhage.

Anti-VEGF therapy have transformed gradually from their use in cancer therapy to being indicated as off-label for management of AMD. Many clinical trials have been performed using systemic administration of anti-VEGF agents. At the angiogenic site, there is a prominent expression of VEGF that is a manifestation of hypoxic condition at the diseased site. Anti-angiogenic agents inhibit neovascularization and vascular permeation by directly binding to the VEGF receptor site as well as circulating VEGF agents. Currently, FDA-approved formulations for treatment of AMD that are available for intravitreal administration are Lucentis™ (Ranibizumab) and Macugen™ (Pegaptanib). Other treatment option includes use Avastin™ (Bevacizumab) as off-label indication and Visudyne™ (Verteporfin) intended for intravenous administration and activation by laser light once the drug reaches eye. However, there is an unmet need for alternative therapies due to narrow therapeutic index, limitation of single dose, rapid clearance, frequent instillation, low therapeutic effectiveness (for systemically administered agents), poor therapeutic outcome and adverse-effects, such as increased intraocular pressure, endophthalmitis and cataract of the currently available therapy. It has been investigated that the use of these agents do not lead to complete remission of disease. However, those investigations have proved effective in decreasing the progression of visual impairment and may improve the visual acuity in many patients. Moreover, the therapeutic effectiveness requires frequent dose instillation using invasive procedures, which may lead to patient non-compliance. Thus, an approach to minimize the dose instillation frequency and delivery at local sites for maximizing therapeutic effectiveness is to be sought for effective management of AMD. Sunitinib malate (SM), a small molecule kinase inhibitor, has been approved for its indication in renal cell carcinoma and gastrointestinal stromal tumors, which targets multiple receptors such as vascular endothelial growth factor receptor (VEGFR), platelet-derived growth factor receptor (PDGFR) and stem cell receptors. However, the use of sunitinib is limited due to the associated severe dose dependent toxicity issues. What is needed is a formula for achieving local SM delivery while minimizing lower dose instillation frequencies. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to compositions and method for treating age-related macular degeneration (AMD). In further aspects, nanoparticles (NPs) (e.g., Poly(lactic-co-glycolic acid) (PLGA)-based NPs) are used in the formulations of drugs due to their biocompatibility, biodegradability, and tailoring release profiles that can have release rates that range from days until months. In a specific aspect, the Sunitinib-loaded nanoparticles disclosed herein provide sustained delivery of the drug at the target side, and the Sunitinib-NPs-incorporated nanogel shows a sustained release profile that can decrease the dosing frequency and improve anti-angiogenesis effects.

Accordingly, in some aspects, disclosed herein is a nanoparticle that comprises a poly (lactic-co-glycolic acid) polymer and sunitinib or a pharmaceutically acceptable salt thereof. In further aspect, disclosed herein is a nanogel drug composition that comprises a nanogel and at least one nanoparticle comprising a poly (lactic-co-glycolic acid) polymer and sunitinib or a pharmaceutically acceptable salt thereof.

In some embodiments, the nanoparticle has a diameter from about 100 nm to about 250 nm.

In some embodiments, the nanogel comprises a thermal reversable nanogel. In some embodiments, the thermal reversable nanogel comprises a methoxy poly (ethylene glycol)-b-polycaprolactone copolymer.

In some aspects, disclosed herein is a pharmaceutical composition that comprises a nanogel drug composition as disclosed herein and a pharmaceutical acceptable carrier.

In some further aspects, disclosed herein is a method of treating age-related macular degeneration in a subject in need thereof that comprises administering to the subject a therapeutically effective amount of a nanoparticle comprising a poly (lactic-co-glycolic acid) polymer and sunitinib or a pharmaceutically acceptable salt thereof. In other aspects, disclosed herein is a method of treating age-related macular degeneration in a subject in need thereof that comprises administering to the subject a therapeutically effective amount of a nanogel drug composition that comprises a nanogel and at least one nanoparticle comprising a poly (lactic-co-glycolic acid) polymer and sunitinib or a pharmaceutically acceptable salt thereof.

In some embodiments, the subject is a human.

In some embodiments, the nanogel drug composition is administered to the subject through intravitreal route.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

The accompanying figures, which are incorporated in and constitute a part of this specification, illustrate several aspects described below.

FIG. 4A shows the Z-average of SM-NPs along with the correlation functional plots. FIG. 4B shows a TEM image of SM-NPs at accelerating voltage of 120 kV with ×40,000 magnification.

FIG. 8A represents cellular uptake of coumarin 6-loaded PLGA NPs into ARPE-19 cells within 2 h of time frame at 37° C. at ×60 magnification (scale bar=40 μm). FIG. 8B shows Relative Mean Fluorescence Intensity (MFI), calculated using Image J software vs time plot for cellular uptake of coumarin 6-loaded PLGA NPs in ARPE-19 cells (*$p<0.05$).

FIG. 9A represents cell migration images of SM solution, SM-NP gel and SM-NPs gel in presence of VEGF 165 (scale bar=1000. FIG. 9B shows wound recovery at 48 hr in comparison to control (untreated) at 0 h for SM solution, SM-NP gel and SM-NPs gel in presence of VEGF at 1 μM and 10 μM concentrations. *** $p<0.001$.

DETAILED DESCRIPTION

Figure 1:
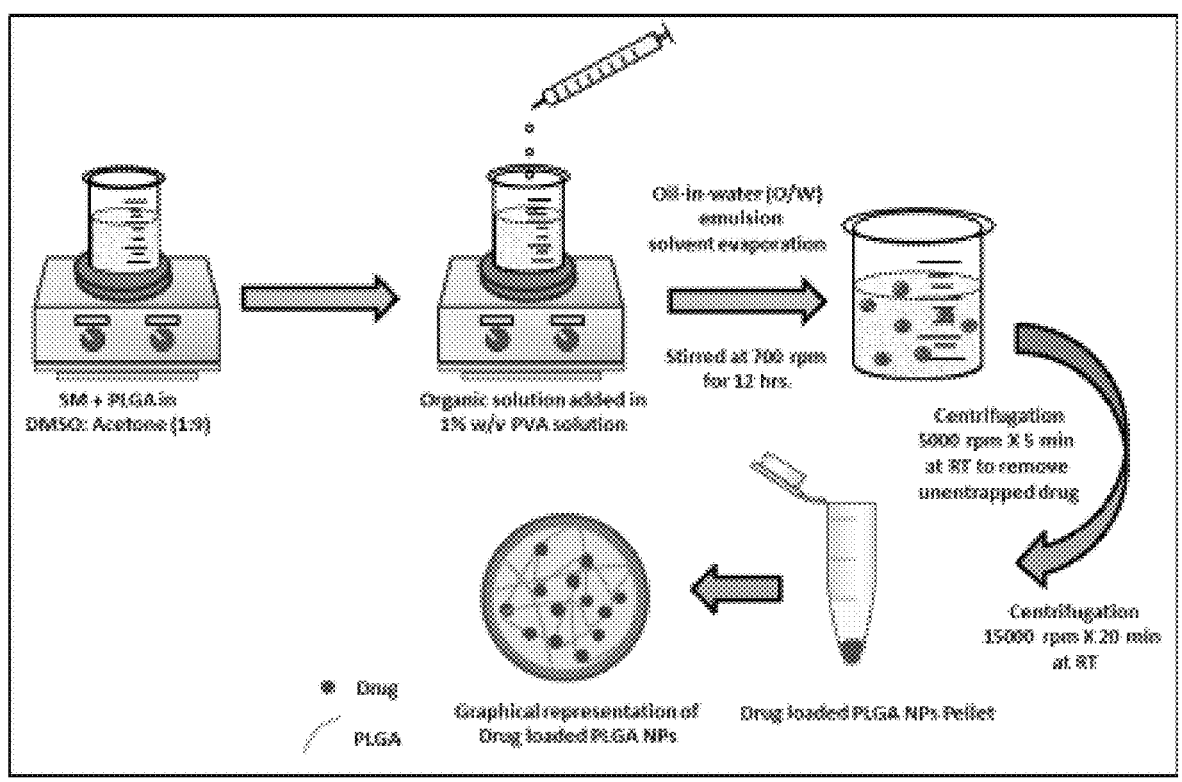
FIG. 1 illustrates a graphical representation of a preparation scheme of sunitinib malate-loaded PLGA nanoparticles using an o/w emulsion solvent evaporation method.

Disclosed herein are nanoparticles, compositions thereof, and methods for treating age-related macular degeneration (AMD). The disclosed nanoparticles comprise a poly (lactic-co-glycolic acid) polymer and sunitinib or a pharmaceutically acceptable salt thereof. The disclosed compositions comprise a nanogel, and at least one nanoparticle comprising a poly (lactic-co-glycolic acid) polymer and sunitinib or a pharmaceutically acceptable salt thereof. The nanogel can comprise a thermal reversible nanogel. The disclosed nanoparticles and nanogels are useful for treating AMD.

Terms used throughout this application are to be construed with ordinary and typical meaning to those of ordinary skill in the art. However, Applicant desires that the following terms be given the particular definition as defined below.

Terminology

As used in the specification and claims, the singular form "a," "an," and "the" include plural references unless the context clearly dictates otherwise. For example, the term "an agonist" includes a plurality of agonist, including mixtures thereof.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

"Administration" to a subject includes any route of introducing or delivering to a subject an agent. Administration can be carried out by any suitable route, for example, any ocular route. In some embodiments, administration is carried out by intraocular route. Administration includes self-administration and the administration by another.

The phrases "concurrent administration", "administration in combination", "simultaneous administration" or "administered simultaneously" as used herein, means that the compounds are administered at the same point in time or immediately following one another.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "biocompatible" generally refers to a material and any metabolites or degradation products thereof that are generally non-toxic to the recipient and do not cause significant adverse effects to the subject.

The term "subject" refers to a human in need of treatment for any purpose, and more preferably a human in need of treatment to treat AMD. The term "subject" can also refer to non-human animals, such as dogs, cats, horses, cows, pigs, sheep and non-human primates, among others.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

Used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

By "reduce" or other forms of the word, such as "reducing" or "reduction," is meant lowering of an event or characteristic (e.g., cell migration). It is understood that this is typically in relation to some standard or expected value, in other words it is relative, but that it is not always necessary for the standard or relative value to be referred to. For example, "reduces cell migration" means decreasing the degrees of cell migration relative to a standard or a control.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

As used herein, the terms "prevent", "preventing" and "prevention" refer to the prevention of the recurrence or the onset of one or more symptoms of a disorder or disease, especially in individuals which have been analyzed to be susceptible or likely to develop the disease.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., AMD). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the treatment of AMD. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "polymer" as used herein refers to a relatively high molecular weight organic compound, natural or synthetic, whose structure can be represented by a repeated small unit, the monomer. Synthetic polymers are typically formed by addition or condensation polymerization of monomers. The polymers used or produced in the present invention are biodegradable. The polymer is suitable for use in the body of a subject, i.e. is biologically inert and physiologically acceptable, non-toxic, and is biodegradable in the environment of use, i.e. can be resorbed by the body. The term "polymer" encompasses all forms of polymers including, but not limited to, natural polymers, synthetic polymers, homopolymers, heteropolymers or copolymers, addition polymers, etc.

The term "copolymer" as used herein refers to a polymer formed from two or more different repeating units (monomer residues). Copolymer compasses all forms copolymers including, but not limited to block polymers, random copolymers, alternating copolymers, or graft copolymers. A "block copolymer" is a polymer formed from multiple sequences or blocks of the same monomer alternating in series with different monomer blocks. Block copolymers are classified according to the number of blocks they contain and how the blocks are arranged.

The term "nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present invention, a nanoparticle typically ranges from about 1 nm to about 1000 nm, preferably from about 50 nm to about 500 nm, more preferably from about 50 nm to about 350 nm, more preferably from about 100 nm to about 250 nm.

As used herein, a "nanogel" refers to a polymer gel composed of synthetic polymers or biopolymers which are chemically or physically crosslinked. In some embodiments, the nanogels are biocompatible. In some embodiments, the nanogels are biodegradable. Methods of obtaining nanogels are known in the art as well as methods for obtaining nanogels that are biocompatible and/or biodegradable (see U.S. Pat. No. 7,727,554 which is incorporated herein by reference in its entirety).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compounds and Methods

In some aspects, disclosed herein is a method of treating age-related macular degeneration (AMD), comprising administering to a subject in need a therapeutically effective amount of a nanogel drug comprising sunitinib or a pharmaceutically acceptable salt thereof.

The details of one or more embodiments of the invention are set forth in the accompanying drawings and the description below. Other features, objects, and advantages of the invention will be apparent from the description and drawings, and from the claims.

In some aspects, disclosed herein is a nanoparticle comprising a poly (lactic-co-glycolic acid) polymer and sunitinib or a pharmaceutically acceptable salt thereof. In some aspects, disclosed herein is a nanogel drug composition, comprising: a nanogel; and at least one nanoparticle comprising a poly (lactic-co-glycolic acid) polymer and sunitinib or a pharmaceutically acceptable salt thereof. The structure of poly (lactic-co-glycolic acid) polymer is shown below:

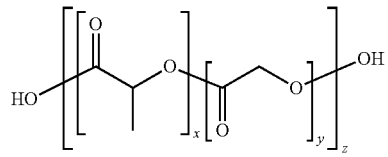

X and y represent the number of times each unit repeats. X can be from 1 to 1000. For example, x can be from 1 to 1000, from 10 to 1000, from 100 to 1000, from 200 to 1000, from 400 to 1000, from 600 to 1000, from 10 to 800, from 50 to 800, from 50 to 500, from 50 to 300, or from 50 to 200. Y can be from 1 to 1000. For example, y can be from 1 to 1000, from 10 to 1000, from 100 to 1000, from 200 to 1000, from 400 to 1000, from 600 to 1000, from 10 to 800, from 50 to 800, from 50 to 500, from 50 to 300, or from 50 to 200.

In some embodiments, the nanoparticle further comprises poly(ethylene glycol) (PEG) and/or polylactide (PLA). Accordingly, in one example, the nanoparticle is a PLA-PEG-PLGA nanoparticle. Nanogels and methods of making the same are known in the art. See, e.g., International Patent Publication NOs: WO2013127949A1 and WO1995003357A1, each of which is incorporated by reference herein in their entireties.

In some embodiments, the nanogel is a thermal reversible nanogel. In one example, the nanogel comprises methoxy poly (ethylene glycol)-b-polycaprolactone. In one example, the nanogel comprises PEG and PLGA.

In some embodiments, the nanoparticle or the nanogel drug composition comprises sunitinib. In some embodiments, the nanoparticle or the nanogel drug composition comprises a pharmaceutically acceptable salt of sunitinib. In one example, the nanoparticle or the nanogel drug composition comprises sunitinib malate. The structure of sunitinib is shown below:

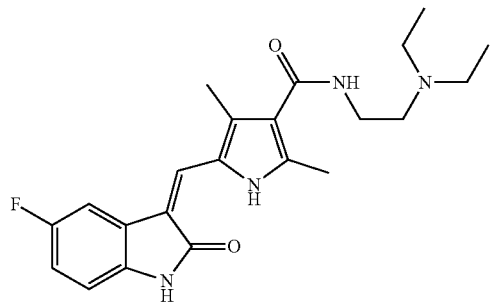 [SMILES: CCN(CC)CCNC(=O)c1c(C)[nH]c(/C=C2\C(=O)Nc3ccc(F)cc32)c1C]

In some embodiments, the nanoparticle has a diameter from about 1 nm to about 1000 nm. In some embodiments, the nanoparticle has a diameter less than, for example, about 1000 nm, about 950 nm, about 900 nm, about 850 nm, about 800 nm, about 750 nm, about 700 nm, about 650 nm, about 600 nm, about 550 nm, about 500 nm, about 450 nm, about 400 nm, about 350 nm, about 300 nm, about 290 nm, about 280 nm, about 270 nm, about 260 nm, about 250 nm, about 240 nm, about 230 nm, about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 90 nm, about 80 nm, about 70 nm, about 60 nm, about 50 nm, about 40 nm, about 30 nm, about 20 nm, or about 10 nm. In some embodiments, the nanoparticle has a diameter, for example, from about 20 nm to about 1000 nm, from about 20 nm to about 800 nm, from about 20 nm to about 700 nm, from about 30 nm to about 600 nm, from about 30 nm to about 500 nm, from about 40 nm to about 400 nm, from about 40 nm to about 300 nm, from about 40 nm to about 250 nm, from about 50 nm to about 250 nm, from about 50 nm to about 200 nm, from about 50 nm to about 150 nm, from about 60 nm to about 150 nm, from about 70 nm to about 150 nm, from about 80 nm to about 150 nm, from about 90 nm to about 150 nm, from about 100 nm to about 150 nm, from about 110 nm to about 150 nm, from about 120 nm to about 150 nm, from about 90 nm to about 140 nm, from about 90 nm to about 130 nm, from about 90 nm to about 120 nm, from 100 nm to about 140 nm, from about 100 nm to about 130 nm, from about 100 nm to about 120 nm, from about 100 nm to about 110 nm, from about 110 nm to about 120 nm, from about 110 nm to about 130 nm, from about 110 nm to about 140 nm, from about 90 nm to about 200 nm, from about 100 nm to about 195 nm, from about 110 nm to about 190 nm, from about 120 nm to about 185 nm, from about 130 nm to about 180 nm, from about 140 nm to about 175 nm, from 150 nm to 175 nm, or from about 150 nm to about 170 nm. In some embodiments, the nanoparticle has a diameter from about 100 nm to about 250 nm. In some embodiments, the nanoparticle has a diameter from about 150 nm to about 175 nm. In some embodiments, the nanoparticle has a diameter from about 135 nm to about 175 nm. The particles can have any shape but are generally spherical in shape.

The molecular weight (MW) of the poly (lactic-co-glycolic acid) polymer can be from about 1,000 Da to about 100,000 Da. For example, the poly (lactic-co-glycolic acid) polymer can have a MW of from about 1,000 Da to about 75,000 Da, from about 1,000 Da to about 50,000 Da, from about 1,000 Da to about 25,000 Da, from about 10,000 Da to about 100,000 Da, from about 10,000 Da to about 75,000 Da, from about 10,000 Da to about 50,000 Da, from about 25,000 Da to about 100,000 Da, from about 25,000 Da to about 75,000 Da, from about 50,000 Da to about 100,000 Da, or from about 50,000 Da to about 75,000 Da.

A nanoparticle has a surface charge that attracts ions having opposite charge to the nanoparticle surface. Such a double layer of ions travels with the nanoparticle. Zeta potential refers to the electrostatic potential at the electrical double layer. A nanoparticle with a zeta potential between, for example, about −10 mV and about +10 mV is considered approximately neutral, while a nanoparticle with zeta potential of greater than, for example, about +10 mV or less than about −10 mV is considered strongly cationic and strongly anionic, respectively. In some embodiments, the nanoparticle disclosed herein has a zeta potential ranging from about −10 mV to about −100 mV, about −20 mV to about −100 mV, about −30 mV to about −100 mV, about −40 mV to about −100 mV, about −50 mV to about −100 mV, about −60 mV to about −100 mV, about −10 mV to about −80 mV, about −20 mV to about −70 mV, about −30 mV to about −60 mV, less than about −5 mV, less than about −6 mV, less than about −7 mV, less than about −9 mV, less than about −10 mV, less than about −11 mV, less than about −12 mV, less than about 13 mV, less than about −14 mV, less than about −15 mV, less than about −16 mV, less than about −17 mV, less than about −18 mV, less than about −19 mV, less than about −20 mV, less than about −21 mV, less than about −22 mV, less than about −23 mV, less than about −24 mV, less than about −25 mV, less than about −26 mV, less than about −27 mV, less than about −28 mV, less than −29 mV. In some embodiments, the nanoparticle disclosed herein has a zeta potential about −10 mV, about −12 mV, about −13 mV, about −14 mV, about −15 mV, about −16 mV, about −17 mV, about −18 mV, about −20 mV, about −22 mV, about −24 mV, about −26 mV, about −28 mV, about −30 mV, about −40 mV, about −41 mV, about −42 mV, about −43 mV, about −44 mV, about −45 mV, about −46 mV, about −47 mV, about −48 mV, about −49 mV, about −50 mV, about −55 mV, about −60 mV, about −70 mV, about −80 mV, about −90 mV, or about −100 mV.

Drug load or loading efficiency refers to the amount of sunitinib or a pharmaceutically acceptable salt thereof (e.g., sunitinib malate) that can be present in the nanoparticle can be from about 0.1% to about 40% (e.g., from about 1% to about 15%) of its nanoparticle weight. For example, the amount of sunitinib or a pharmaceutically acceptable salt thereof present in the nanoparticle can be from about 0.1%, about 0.2%, about 0.3%, about 0.4%, about 0.5%, about 0.6%, about 0.7%, about 0.8%, about 0.9%, about 1%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 15%, about 16%, about 17%, about 18%, about 19%, about 20%, about 22%, about 24%, about 26%, about 28%, about 30%, about 32%, about 34%, about 36%, about 38%, or about 40% of its nanoparticle weight.

In some embodiments, the nanoparticle is in a nanogel drug composition comprising a nanogel. Incorporating nanoparticles into a nanogel matrix can prolongs a therapeutic effect in a targeted tissue (e.g., eye).

In some embodiments, the nanogel comprises a thermal reversable nanogel. In some embodiments, the thermal reversable nanogel comprises a methoxy poly (ethylene glycol)-b-polycaprolactone copolymer. The concentration of the methoxy poly (ethylene glycol)-b-polycaprolactone copolymer-based nanogel can be, for example, about 10% w/v, about 11% w/v, about 12% w/v, about 13% w/v, about 14% w/v, about 15% w/v, about 16% w/v, about 17% w/v, about 18% w/v, about 19% w/v, about 20% w/v, about 21% w/v, about 22% w/v, about 23% w/v, about 24% w/v, about 25% w/v, about 26% w/v, about 27% w/v, about 28% w/v, about 29% w/v, about 30% w/v, about 31% w/v, about 32% w/v, about 33% w/v, about 34% w/v, about 35% w/v, about 36% w/v, about 37% w/v, about 38% w/v, about 39% w/v, about 40% w/v, about 41% w/v, about 42% w/v, about 43% w/v, about 44% w/v, about 45% w/v, about 46% w/v, about 47% w/v, about 48% w/v, about 49% w/v, about 50% w/v, about 55% w/v, or about 60% w/v.

Nanoparticles, as described herein, can be synthesized or assembled via any suitable process. Preferably, the nanoparticles are assembled in a single step to minimize process variation. A single step process can include nanoprecipitation and self-assembly. The nanoparticles can be synthesized or assembled by dissolving or suspending the sunitinib in an organic solvent, preferably a solvent that is miscible in an aqueous solvent used for precipitation. In certain examples, acetonitrile is used as the organic solvent, but any suitable solvent can be used. Hydrophilic components are dissolved in a suitable aqueous solvent, such as water, 4 wt % ethanol, or the like. The organic phase solution can be added drop wise to the aqueous phase solution to nanoprecipitate the sunitinib and allow self-assembly of the nanoparticle in the aqueous solvent.

The nanoparticles disclosed herein can further comprise one or more therapeutic agents, including, for example, one or more anti-inflammatory agents. In some embodiments, the anti-inflammatory agents can comprise triamcinolone acetonide and/or loteprednol etabonate.

In some embodiments, the nanogel disclosed herein can further comprise a nanoparticle comprising an anti-inflammatory agent. In some embodiments, the anti-inflammatory agent comprises triamcinolone acetonide and/or loteprednol etabonate.

In some aspects, disclosed herein is a pharmaceutical composition comprising the nanoparticles or nanogel drug composition disclosed herein and a pharmaceutical acceptable carrier.

In some aspects, disclosed herein is a method of treating AMD in a subject in need thereof, comprising administering to the subject a therapeutically effective amount of a nanoparticle comprising a poly (lactic-co-glycolic acid) polymer and sunitinib or a pharmaceutically acceptable salt thereof. In other aspects, disclosed herein is a method of treating AMD in a subject in need thereof, comprising administering to the subject a therapeutically effective amount of a nanogel drug composition comprising a nanogel and at least one nanoparticle, wherein the nanoparticle comprises a poly (lactic-co-glycolic acid) polymer, and sunitinib or a pharmaceutically acceptable salt thereof.

In some embodiments, the subject is a human. In some embodiments, the human has AMD. In some embodiments, the human is suspected to have AMD.

The term "age-related macular degeneration" or "AMD" used herein refers to an eye disease and/or disorder that leads to vision loss in elderly people. Macular degeneration results in a break down the macula, the light-sensitive part of the retina responsible for the sharp, direct vision needed to read or drive. Central vision is especially affected. Macular degeneration is diagnosed as either dry (atrophic) or wet (exudative). Macular degeneration can produce a slow or sudden painless loss of vision. AMD-associated damage to the epithelial layer of the retina triggers secretion of cytokines such as vascular endothelial growth factors (VEGF), causing ion channel dysfunction and abnormal lipid metabolism that lead oxidative damage to cells. To compensate for the decrease blood supply at retinal region, neovascularization occurs that may lead to increased risk of fluid deposition, inflammation, vascular occlusion and hemorrhage. Accordingly, it should understood herein and contemplated that each of the above noted symptoms, including, such as, breakdown of macula, loss of vision (especially central vision), depositing of pigment in the macula, damage to epithelial layer of retina, increased levels of inflammation in the eye (e.g., increased levels of vascular endothelial growth factors (VEGF), ion channel dysfunction and abnormal lipid metabolism, elevated oxidative damage to cells in the eye), and increased neovascularization of cells at retina and/or macula, are all within the definition of "age-related macular degeneration" or "AMD".

Accordingly, it should be understood herein that a treatment of AMD may be a treatment of one or more of breakdown of macula, loss of vision (especially central vision), depositing of pigment in the macula, damage to epithelial layer of retina, increased levels of inflammation in the eye (e.g., increased levels of vascular endothelial growth factors (VEGF), ion channel dysfunction and abnormal lipid metabolism, elevated oxidative damage to cells in the eye), and increased neovascularization of cells at retina and/or macula. Treatment can be monitored and evaluated by examination of the back of the eye, test for defects in the central center, fluorescein angiography, indocyanine green angiography, and/or optical coherence tomography, wherein a mitigation of AMD following the treatment disclosed herein can be indicated by improvement of vision. It should be understood and herein contemplated that the terms "increase" and "decrease" used herein refers to an increase or decrease as compared with the condition prior to the treatment of the subject or as compared with incidence of such symptom in a general or study population.

"VEGF" or vascular endothelial growth factor refers to an angiogenic factor. VEGF was initially characterized by its actions on the vasculature, inducing vasculogenesis, angiogenesis, and increased permeability of capillary vessels. It is regulated in many tumors and its contributions to tumor angiogenesis has been well defined. In some embodiments, the VEGF polypeptide is that identified in one or more publicly available databases as follows: HGNC: 12680, Entrez Gene: 7422, Ensembl: ENSG00000112715, OMIM: 192240, UniProtKB: P15692.

In some embodiments, the nanoparticles or nanogel drug composition are administered to the subject through intravitreal or intraocular route.

The disclosed methods can be performed any time prior to and/or after the onset of AMD. In some aspects, the disclosed methods can be employed 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 years;12, 11, 10, 9, 8, 7, 6, 5, 4, 3, 2, or 1 months; 30, 29, 28, 27, 26, 25, 24, 23, 22, 21, 20, 19, 18, 17, 16, 15, 14, 13, 12, 11, 10, 9, 8, 7, 6, 5, 4, or 3 days; 60, 48, 36, 30, 24, 18, 15, 12, 10, 9, 8, 7, 6, 5, 4, 3, or 2 hours prior to the onset of AMD; or 1, 2, 3, 4, 5, 6, 7, 8, 9, 10, 15, 20, 25, 30, 35, 40, 45, 50, 55, 60, 75, 90, 105, 120 minutes; 3, 4, 5, 6, 7, 8, 9, 10, 11, 12, 15, 18, 24, 30, 36, 48, 60 hours; 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days; 4, 5, 6, 7, 8, 9, 10, 11, 12 or more months; 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 years after the onset of AMD.

The present disclosure shows that the nanoparticle or the nanogel drug composition described herein can slow down the release of Sunitinib or a pharmaceutically acceptable salt thereof. In some embodiments, Sunitinib or a pharmaceutically acceptable salt thereof is present in an amount sufficient to maintain a release or delivery of Sunitinib or a pharmaceutically acceptable salt thereof from the nanoparticle or the nanogel drug composition to a target site of an eye or close proximity thereof, upon administration, at a therapeutically effective amount over a specified period of time, over a period of more than 1 month, including, e.g., at least about 2 months, at least about 3 months, at least about 6 months, at least about 12 months or longer. Such amounts of Sunitinib or a pharmaceutically acceptable salt thereof dispersed or encapsulated in the nanoparticle or in the nanogel drug composition disclosed herein can be generally smaller, e.g., at least about 10% smaller, than the amount of Sunitinib or a pharmaceutically acceptable salt thereof present in the current dosage of the treatment regimen (i.e., without nanoparticle or nanogel drug composition) required for producing essentially the same therapeutic effect. Indeed, Sunitinib or a pharmaceutically acceptable salt thereof encapsulated in, or adhered to, a nanoparticle or a nanogel drug composition can potentially increase duration of the therapeutic effect for Sunitinib or a pharmaceutically acceptable salt thereof. Stated another way, encapsulating Sunitinib or a pharmaceutically acceptable salt thereof in a nanoparticle or a nanogel composition or adhering Sunitinib or a pharmaceutically acceptable salt thereof to the nanoparticle or the nanogel composition can increase its therapeutic efficacy, i.e., a smaller amount of Sunitinib or a pharmaceutically acceptable salt thereof encapsulated in a nanoparticle, as compared to the amount present in a typical one dosage administered for a particular ocular condition (e.g., age-related macular degeneration), can achieve essentially the same therapeutic effect. Accordingly, the nanoparticle or the nanogel drug composition can comprise Sunitinib or a pharmaceutically acceptable salt thereof in an amount which is less than the amount traditionally recommended for one dosage of Sunitinib or a pharmaceutically acceptable salt thereof, while achieving essentially the same therapeutic effect. For example, if the traditionally recommended dosage of Sunitinib or a pharmaceutically acceptable salt thereof is X amount then the nanoparticle or the nanogel drug composition can comprise Sunitinib or a pharmaceutically acceptable salt thereof in an amount of about 0.9×, about 0.8×, about 0.7×, about 0.6×, about 0.5×, about 0.4×, about 0.3×, about 0.2×, about 0.1× or less. Without wishing to be bound by the theory, this can allow administering a lower dosage of Sunitinib or a pharmaceutically acceptable salt thereof in a nanoparticle to obtain a therapeutic effect which is similar to when a higher dosage is administered without the nanoparticle or the nanogel drug composition. Low-dosage administration of Sunitinib or a pharmaceutically acceptable salt thereof can reduce side effects of Sunitinib or a pharmaceutically acceptable salt thereof, if any, and/or reduce likelihood of the subject's resistance to Sunitinib or a pharmaceutically acceptable salt thereof after administration for a period of time.

In some embodiments, the dosing frequency of Sunitinib or a pharmaceutically acceptable salt thereof that is formulated in the nanoparticle or the nanogel composition disclosed herein is less (e.g., about 2-fold less, about 3-fold less, about 4-fold less, about 5-fold less, about 6-fold less, about 7-fold less, about 8-fold less, about 9-fold less, about 10-fold less, about 15-fold less, about 20-fold less, about 30-fold less, about 40-fold less, or about 50-fold less) than the dosing frequency of Sunitinib or a pharmaceutically acceptable salt thereof when Sunitinib or a pharmaceutically acceptable salt thereof is administered without the nanoparticle or the nanogel composition.

Dosing frequency for the nanoparticle or the nanogel drug composition disclosed herein, includes, but is not limited to, at least once every 12 months, once every 11 months, once every 10 months, once every 9 months, once every 8 months, once every 7 months, once every 6 months, once every 5 months, once every 4 months, once every 3 months, once every two months, once every month; or at least once every three weeks, once every two weeks, once a week, twice a week, three times a week, four times a week, five times a week, six times a week, or daily. In some embodiments, the interval between each administration is less than about 4 months, less than about 3 months, less than about 2 months, less than about a month, less than about 3 weeks, less than about 2 weeks, or less than less than about a week, such as less than about any of 6, 5, 4, 3, 2, or 1 day. In some embodiments, the dosing frequency for the nanoparticle or the nanogel drug composition includes, but is not limited to, at least once a day, twice a day, or three times a day. In some embodiments, the interval between each administration is less than about 48 hours, 36 hours, 24 hours, 22 hours, 20 hours, 18 hours, 16 hours, 14 hours, 12 hours, 10 hours, 9 hours, 8 hours, or 7 hours. In some embodiments, the interval between each administration is less than about 24 hours, 22 hours, 20 hours, 18 hours, 16 hours, 14 hours, 12 hours, 10 hours, 9 hours, 8 hours, 7 hours, or 6 hours. In some embodiments, the interval between each administration is constant. For example, the administration can be carried out daily, every two days, every three days, every four days, every five days, or weekly. Administration can also be continuous and adjusted to maintaining a level of the compound within any desired and specified range.

EXAMPLES

It is intended that the invention not be limited to the particular implementations disclosed herein, but that the invention will include all implementations falling within the scope of the appended claims.

Example 1. An In Vitro Assessment of Thermo-Reversible Gel Formulation Containing Sunitinib Nanoparticles for Neovascular Age-Related Macular Degeneration Materials. SM was purchased from Selleck Chemicals (Houston, Tex., USA). PLGA (50:50 lactide glycolide/MW 19000) [Catalogue number (CN): AC436200010], PLGA was purchased from Acros Organics (NJ, USA). Dialysis membrane (MWCO: 12,000 Da) [CN: D6191] and Coumarin 6 dye were purchased from Sigma Aldrich (St. Louis, Mo.). Poly(vinyl alcohol) (Mw 100,000, 87% hydrolysed) [CN: 593328] was obtained from Fisher Scientific (USA). AK036—Methoxy poly (ethylene glycol)-b-poly (caprolactone) (Mw 750:2,500 Da) poly-vivo thermo gel was purchased from PolySciTech IN, USA. Fetal Bovine Serum (FBS) [CN: 10437028] and Penicillin-streptomycin (10,000 U/ml) [CN: 15140122] were obtained from Gibco Thermo Fisher Scientific, USA. 3-(4, 5-dimethylthiazol-2-yl)-2, 5-diphenyltetrazolium bromide salt (MTT reagent) [CN: 5224], and nucleus stain DAPI (4', 6-diamidino-2-phenylindole) [CN: 5748] were purchased from Tocris Bioscience (MN, USA). Cell Mask™ deep red plasma stain [CN: C10046] was purchased from molecular probes, Invitrogen™ Thermo Fisher Scientific, USA. Pierce BCA protein assay kit [CN: 23225] and Invitrogen™ eBioscience™ Human VEGF-A Platinum ELISA Kit [CN: 50-182-08] were purchased from fisher scientific, USA. ARPE-19, a human retinal pigment epithelial cell line (ATCC® CRL2302™) and Dulbecco's Modification of Eagle's Medium F 12 (DMEM F12) (ATCC® 30-2006™) were purchased from American Type Culture Collection (ATCC) (VA, USA). Cell culture Phosphate Buffer Saline (1×) (PBS) [CN: MT21040CV] was ordered from Corning Cellgro (Manassas, Va.). Trypsin (0.05%) [CN: 25300054] was ordered from Thermo Fisher (Lansing, Mich.). All other analytical reagent grade chemicals were used without performing any added purification.

Cell culture. ARPE-19, a human retinal pigment epithelial cell line (ATCC® CRL2302™) cells were grown and maintained in DMEM F12 medium supplemented with 10% v/v FBS and 1% 10,000 U/ml penicillin-streptomycin antibiotics. The cell cultures were allowed to incubate at 37° C. temperature, in a humidified atmosphere with 5% $CO_2$.

Preparation of Sunitinib Malate loaded PLGA NPs (SM-NPs). SM-NPs were prepared by o/w emulsion solvent evaporation method. A schematic representation of preparation procedure is provided in FIG. 1. Briefly, Drug: Polymer [PLGA (50:50 lactide glycoside, M.W approx.

19000)] were taken at optimized weight ratio of 1:7 and dissolved in 2 ml of dimethyl-sulfoxide (DMSO): Acetone ratio of 1:9 as organic phase. This organic solution was slowly added in 3 ml of 1% w/v PVA solution using 23G syringe under continuous stirring on magnetic stirrer (Thermo Fisher, Lansing, Mich.). The resulting emulsion was stirred overnight at 700 rpm for evaporation of organic solvent. The nanoparticulate suspension obtained was centrifuged first at 5000 rpm for 5 min at room temperature (RT) to remove unentrapped drug followed by centrifuging the supernatant at 18000 rpm for 20 min at RT. The nanoparticle pellet was collected, washed thrice with distilled water and re-suspended in saline. Placebo nanoparticles and Coumarin 6 loaded nanoparticles (by loading dye instead of drug) were formulated using similar procedure.

Thermal analysis of pure SM, physical mixture of SM and PLGA and SM-NPs was performed using TA Instruments DSC Q 20 (TA Instruments, New Castle, Del. USA, Q series Q20-2288-DSC software). 5 mg of all the three samples were individually placed in an aluminium pan and hermetically sealed. The samples were then separately heated from 30° C. to 300° C. at a rate of 10° C. min-1 in a nitrogen atmosphere at a flow of 50 mL/min. As a reference, empty aluminum pan was utilized.

Physicochemical Characterization. Physicochemical characterization of developed nanoparticles was carried out using Fourier transform infrared spectroscopy (FTIR) and differential scanning calorimetry (DSC) techniques. FTIR was done to determine the presence of and types of functional groups in SM. The interaction between the SM and polymer composition as well as encapsulation of SM in nanoparticles was analyzed by FTIR using UATR Two FTIR Spectrometer (PerkinElmer, Waltham, Mass., PerkinElmer spectrum software) at a scanning range of 400-4000 cm$^{-1}$. Pure drug, polymer, physical mixture of drug and polymer, and SM-NPs were investigated, and background scans were taken after each triplicate to constitute atmospheric conditions. The results were graphed as a radiation plot of percent transmission through the molecule versus the wavenumber of the detected radiation (cm$^{-1}$). Thermal analyses of pure SM, physical mixture of SM and PLGA, and SM-NPs were performed using TA Instrument DSC Q-20 (TA Instruments, New Castle, Del. USA, Q series Q20-2288-DSC software). Five milligrams of all the three samples was individually placed in an aluminum pan and hermetically sealed. The samples were then separately heated from 30° C. to 300° C. at a rate of 10° C. min$^{-1}$ in a nitrogen atmosphere at a flow of 50 mL/min. As a reference, an empty aluminum pan was utilized.

Particle size and Zeta potential of nanoparticles. Particle size of nanoparticles was detected based on the dynamic light scattering technique (DLS) using Nano ZS90 (Malvern Instruments Ltd., UK, Zeta Sizer Software Ver. 7.10) having scattering angle of 90° and 633 nm He—Ne laser light source. At temperature of 25° C., the size analysis of sample was carried out in triplicate after ten times dilution using double distilled water. Z-average and polydispersity index (PDI) were reported as a result.

Zeta potential of nanoparticles was determined based on Smoluchowski equation that considers electrophoretic mobility of the nanoparticles and their back-scatter at 90°. The analysis was carried out in triplicate after ten times dilution of nanoparticles using double distilled water using zeta cuvette and Zeta Sizer Nano ZS 90 (Malvern Instruments Ltd., UK, Zeta Sizer Software Ver. 7.10).

Transmission Electron Microscope. Morphology, shape and size of the SM-NPs were observed using transmission electron microscope (TEM) (JEOL JEM 1400 electron microscope with Gaton camera, Peabody, Mass., USA). The adequate volume of dispersed nanoparticle sample was retained on EMS formvar support film square grid, 200 Cu, and allowed to air dry for 10 min. Afterwards, it was treated with 2% w/v phosphotungstic acid for negative staining. The samples were visualized with 40,000 magnifications at accelerating voltage of about 120 kV.

Entrapment efficiency. The prepared nanoparticles were centrifuged at 5000 rpm for 5 min to remove the unentrapped drug followed by centrifugation at 18000 rpm for 20 min to collect the nanoparticulate pellet from the bottom of the Eppendorf tubes. The process was carried out at room temperature. The collected pellet was washed thrice with distilled water to remove traces of free drug that may be adsorbed on the surface. To determine entrapment efficiency and loading efficiency, reconstituted nanoparticles were treated with methanol to extract the loaded SM drug and were quantified using UV spectroscopy (Model: S-2150UV; Cole Parmer Instrument Company) at 432 nm (λmax) in methanol.

$$\% \text{ Entrapment efficiency} = \frac{\text{Amount of drug loaded in nanoparticles}}{\text{Actual amount of drug used for nanoparticles preparation} \times 100}$$

$$\% \text{ Loading Efficiency} = \frac{\text{Amount of SM in nanoparticles}}{\text{Total amount of nanoparticles} \times 100}$$

Preparation of SM-NPs incorporated thermo-reversible gel (SM-NP gel), Thermo-reversible gels (TR) were prepared by slowly dispersing the polymer in aqueous phase in cold condition. To prepare gel, Methoxy Poly (ethylene glycol)-b-Polycaprolactone copolymers/mPEG-PCL (MW ~750-2500 Da, PolySci Tech) polymer was solubilized in distilled water by stirring at 350 rpm at 4° C. overnight. The gel was then heated at 80° C. for half an hour which can cause break-down of the crystalline domains in PCL. To equilibrate, later on the gel was allowed to stir back to 4° C. at 350 rpm overnight. The phase transition and formation of gel based on change of temperature was studied. For that aqueous solutions of the gel with various concentrations were prepared (10, 20, 30 and 40% w/v) and they were heated from 10 to 60° C. individually. At an interval of each 2° C., the tubes were overturned to examine flow. Following tube inversion, if there is no flow observed, it can be concluded that the solution has achieved gel state. Prepared SM-NPs were suspended in above TR gel (SM-NP Gel) at 2-8° C. in cold room and gelation temperature was detected by visual inspection.

In vitro drug release study. The in vitro drug release study for SM from nanoparticles and nanoparticles incorporated thermo-reversible gel were compared with plain drug solution and was studied at 37°±0.5° C. In short, drug solution in DMSO, SM-NPs and SM-NP Gel having equivalent quantity of SM (1 mg/ml) were placed in dialysis tubes (MWCO 10 KDa) and sealed tightly by using dialysis closures. Then, the dialysis tubes were immersed in 20 ml of PBS (pH 7.4) as a release medium comprising of 0.1% Tween 80 (v/v). Release medium was allowed to stir at 150 rpm and the 0.5 mL of samples were withdrawn at 0.25, 0.5, 1, 2, 4, 6, 12, 24, 48, 72, 96, 120, 144 and 168 h. The volumes were made up with fresh release medium after each sampling. The concentration of SM in a sample was determined by UV spectroscopy at 432 nm after dilution with methanol in ratio of 1:10. For all the formulations, in vitro release tests were carried out in triplicate and results were described as cumulative quantity of drug released at each point of time.

Cytotoxicity study. The MTT assay was carried out to determine cytotoxicity of SM-NPs as well as in SM-NPs gel in comparison with pure drug solution, in ARPE-19, human retinal pigment epithelial cells. The cells were seeded in 200 µl of DMEM F12 supplemented with 10% FBS in a 96 well plate (Corning, N.Y.) at a seeding density of 5000 cells/well and incubated for 24 h at 37° C., 5% $CO_2$ atmosphere to allow attachment and growth of the cells. SM drug solution and formulations with various concentrations of SM were prepared by first dissolving SM in DMSO and then diluting them with DMEM F12 medium without FBS. The cells were treated with formulations after 24 h of seeding and incubated for 4 h. After 4 h, the treatment was removed from the cell well and cells were washed one time with sterile 1×PBS to ensure removal of treatment. The cells were then incubated after adding fresh DMEM F12 medium having 10% FBS at 37° C., 5% $CO_2$ atmosphere for 24 h and 48 h. After 24 h & 48 h, the media was replaced by 100 µl of MTT reagent solution (1 mg/mL) to each well and kept at 37° C., 5% $CO_2$ atmosphere for 4 h. After 4 h the MTT reagent was removed and 100 µl of DMSO (Sigma Aldrich, USA) was added to each well to allow dissolution of formed formazan crystals. Intensity of color produced after dissolution of formazan crystals was quantified by measuring optical density at 595 nm wavelength by microtiter plate reader (Spectra MAX 190, Molecular Devices, California, USA). For positive and negative controls, cells were treated with 0.1% Triton X and DMEM F12, respectively. Cell viability were calculated graphically from concentration vs viability curves, considering the optical density of control well as 100% viable.

Cellular uptake using confocal microscope. To access the cell uptake potential of the nanoparticles and for determining the localization in cell, confocal microscopy was carried out using ARPE-19 cells. All the formulations that includes drug formulations, coumarin formulation and blank were prepared as outlined above. The ARPE-19 cells were seeded at $2×10^5$ density per well in six well plate and incubated for a day to achieve 70% confluency. The cell monolayer was then washed with PBS three times to remove suspended dead cells and aspirated. Each well was treated with the formulation i.e. coumarin 6 loaded nanoparticles along with placebo nanoparticles for comparison (blank). The incubation was carried out with the formulations for period of 4 h and subsequently the medium of well aspirated and washed with PBS thrice and fixed with 4% paraformaldehyde. DAPI was added to the cells for nuclear staining followed by CellMask™ deep red plasma stain for membrane staining and examined under confocal microscope FV1200 (Olympus, Tokyo, Japan) at ×60 magnification.

Wound scratch assay. Wound healing assay was performed as per the earlier reports to analyse the inhibitory effect of SM and its formulation on VEGF165 (rhVEGF; R&D Systems) induced angiogenesis. ARPE-19 cells were seeded and allowed to grow to attain 80% confluency in 24-well plates. Carefully, wounds were made by pipette tip to take out monolayer of cells as a strip. The wounds were created typically with around 300 µm of the average size and 5% or more variation in wound width was considered for the study. To ensure removal of partially adhered cells on the plates due to creation of the wound, they were washed with sterile PBS twice. The cell wells were then treated with at 1 µM and 10 µM concentrations of SM-NP gel formulations in DMEM F12 media without FBS. Cell migration was observed by using ZEISS inverted phase contrast microscope, (Axicom 506 mono) with Axicom MRCS-ZEN2pro software and quantified by calculating the area covered by the cells because of cell migration from the wound edges towards the center area of the wound using ImageJ software. To check the effect of presence of VEGF on the cell migration, two wells were also kept at above two concentrations and treated with VEGF simultaneously. Further, one well consisted of complete medium and one was treated with VEGF acted as reference and controls respectively. Incubation was done for 48 h at 37° C. in 5% $CO_2$ atmosphere. The treated formulations were removed after incubation and the cells were washed with sterile 1×PBS thrice to ensure removal of treatment. The cells were then treated 4% paraformaldehyde solution to fix them and were imaged. The width of the wound was measured using images captured by microscope. Width of the untreated wound at 0 h was taken as 100% and considered as reference and % area covered for each wound was compared in relation to reference one.

VEGF inhibition using ELISA. Human retinal pigmented epithelium ARPE-19 cells were seeded in 24 well plate at density of $5×10^4$ cells/mL and allowed to grow for 24 h in DMEM F12 medium supplemented with 10% FBS and were incubated at 37° C., 5% $CO_2$ atmosphere till wells became confluent. After 24 h, the culture media was replaced by incomplete media which is DMEM F12 without FBS and treatment with formulation was given. The treatment group consisted of free drug solution, SM-NPs and SM-NP gel, each at equivalent to 10 µM SM concentration and were further incubated for a total period of 48 hours. Quantification of the VEGF secretion in the culture media was done by ELISA method using Human VEGF-A Platinum ELISA Kit following manufacturer's instructions. The protein content in the cells were estimated using Pierce BCA protein assay kit after collecting cell lysate and the by normalizing VEGF secretion to total protein. Samples were read using ELISA plate reader (Spectra MAX 190, Molecular Devices, California, USA) at 450 nm absorbance and 550 nm and difference was recorded, followed by calculating inhibition of VEGF secretion using standard curve.

Statistical analysis All analyses have been performed in triplicate and data are represented as mean±standard deviation, unless otherwise mentioned. Statistical data analysis was implemented using ANOVA and Student's t-test. GraphPad Prism (Version 6, USA) was used for all analyses and p-value reported at level of $<0.05$; $<0.01$ or $<0.001$ at each place.

Results

Nanoparticles (NPs) have been investigated in the formulation of drugs due to their biocompatibility, biodegradability and tailoring release profiles that may range from days till months. Poly(lactic-co-glycolic acid) (PLGA) in product is approved by FDA to be used clinically and it is biocompatible, as well as biodegradable. Considering the ease of translation of PLGA-based product due to biocompatibility and biodegradability, PLGA were selected for the development of nanoparticles. Ophthalmic SM loaded biocompatible PLGA nanoparticle (SM-NPs) can provide sustained delivery of drug at target site and SM-NPs incorporated thermo-reversible gel shows superior sustained release profile which can decrease the dosing frequency as well as shows anti-angiogenic effect. The objective of this investigation is to formulate sustained release formulation of SM-NPs incorporated thermo-reversible gel (SM-NPs gel) and to evaluate the formulation using physiochemical methods and cell-based assays. The SM-NPs gel formulation possessed a unique property of syringeability when at or below room temperature and turned to gel form at body temperature. Thus, the residence time of the formulation increases after injection, lead to a slower release of drug at the target site and further decrease the dosing frequency. The thermo-reversible characteristic of gel can aid in handling of the product prior to use and improve patient compliance.

Figure 2:
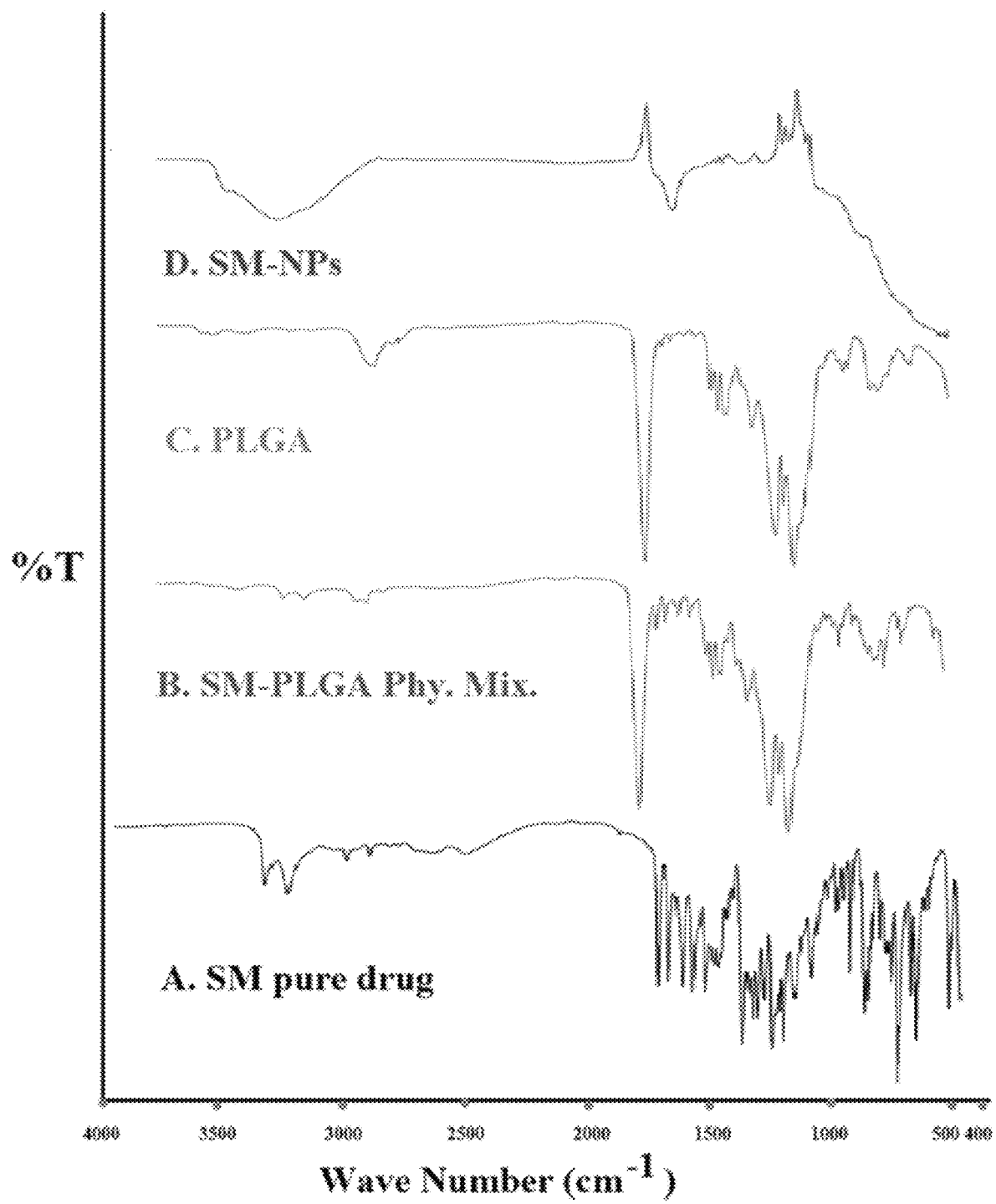
FIG. 2 contains the FTIR spectra of (spectrum A SM pure drug, (spectrum B) SM and PLGA physical mixture, (spectrum C) PLGA, and (spectrum D) SM-NPs.

Physicochemical characterization. Pure SM drug, PLGA alone, physical mixture of SM and PLGA, and SM-NPs were investigated for physicochemical characterization using FTIR and DSC techniques. To study the compatibility of SM with PLGA and to confirm entrapment of SM in formed NPs, FTIR analysis was performed (FIG. 2). FTIR Spectra of PLGA 50:50 displayed major peaks such as 3465 $cm^{-1}$, 3325 $cm^{-1}$, between 2979-2627 $cm^{-1}$, between 1700-1850 $cm^{-1}$ and between 1050-1250 $cm^{-1}$. Pure SM drug exhibited strong absorption bands and the principle peaks were observed at 3322 $cm^{-1}$, 2979 $cm^{-1}$, 2884 $cm^{-1}$, 1669 $cm^{-1}$, and 1026 $cm^{-1}$. Table 1 shows all the major peaks obtained at particular wavenumber for PLGA and SM drug individually and corresponding groups. These characteristic peaks are retained in the physical mixture of SM drug with PLGA with a broadening effect and a decrease in intensity of principal peaks. Whereas, in case of SM NPs formulation, all characteristic pertaining to SM were absent, indicating the complete encapsulation of drug in the NPs and only a diffused peak throughout the spectra at wavenumber higher than 1300 $cm^{-1}$ was observed in FIG. 2.

TABLE 1

FTIR peaks of PLGA polymer and SM at specific wavenumber with corresponding groups

| Sample Material | Wavenumber ($cm^{-1}$) | Corresponding group |
| --- | --- | --- |
| PLGA | 3465 and 3325 | O—H |
| | 2979-2627 | C—H, C—$H_3$ and C—$H_2$ |
| | 1700-1850 | carbonyl-C=O |
| | 1050-1250 | C—O |
| SM drug | 3322 | O—H (acid), N—H |
| | 2979 | HC=CH (aryl) |
| | 2884 | C—H (alkyl) |
| | 1669 | —NH—C=O |
| | 1026 | C—F |

Figure 3:
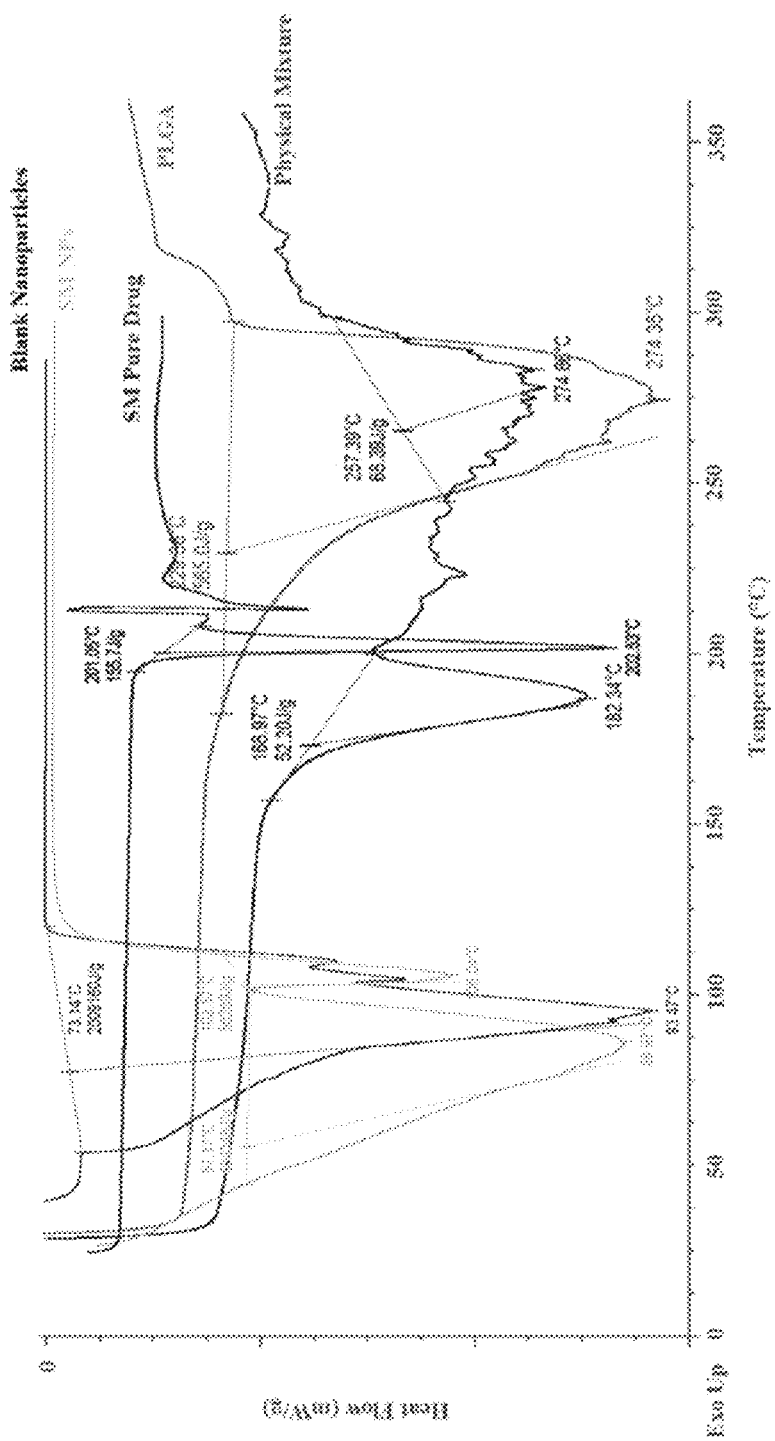
FIG. 3 shows DSC spectra of SM (sunitinib malate), PLGA, physical mixture, blank nanoparticles, and sunitinib malate nanoparticle formulation.

FIG. 3 shows thermal analysis of SM, PLGA, physical mixture, blank NPs, and SM-NPs using DSC technique. The nature as well as the physical state of encapsulated drug in polymer matrix can have an effect on its release and thus DSC thermograms enabled to identify the nature. SM show sharp endothermic peak at around 202° C. which indicated its characteristic melting point. That peak was absent in DSC spectrum for SM-NPs confirming the entrapment of SM in NPs and presence of SM as amorphous form. However, the characteristic endothermic peak of SM was present in DSC spectrum of physical mixture of SM and PLGA.

Figure 4A:
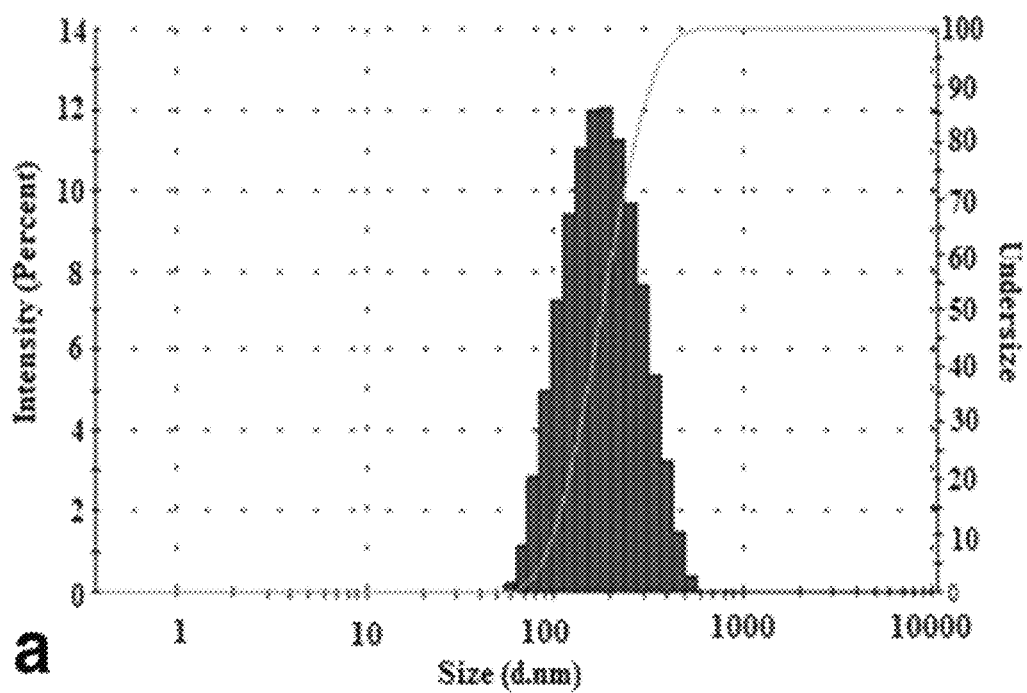
FIG. 4A and FIG. 4B show parameters of SM-NPs.

Particle size and Zeta potential. The size and PDI of SM-NPs was measured using DLS technique and was found to be of the order of 164.5±5.8 nm with PDI of 0.154±0.008. The low PDI of the SM-NPs exhibited the dispersion homogeneity and uniform distribution of particle size of the nanoparticles. The mean zeta potential of SM-NPs was determined using a Malvern Zetasizer Nano ZS90 and was −18.27±3.6 mV for the SM NPs. FIG. 4A shows Z-average along with the correlation functional plots for SM-NPs.

Figure 4B:
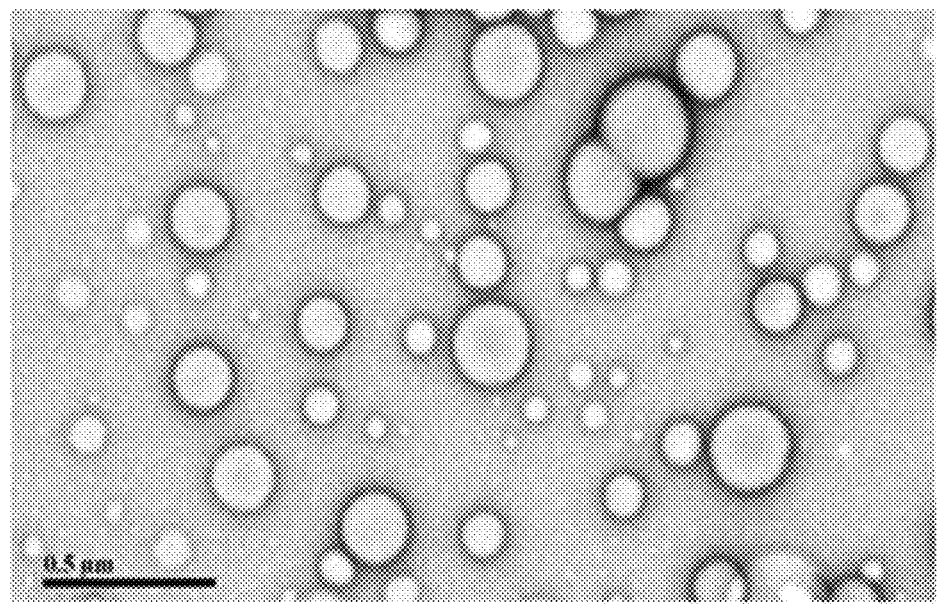

Transmission Electron Microscope. The TEM study showed particle size for the formulated SM NPs were 140±11 nm (FIG. 4 B). It can be noted that the obtained size shows the actual size of nanoparticle as opposed to the size obtained using Zetasizer that measures the hydrodynamic size of particles. TEM images demonstrated nanoparticles of uniform size and were in concurrence with the DLS results and were spherical with smooth surface.

Encapsulation Efficiency. Entrapment efficiency was calculated by centrifuging the NPs and resuspending the NPs pellet in methanol. Entrapment efficiency was found 72.0%±3.5%. Percent drug loading was found to be 9%±0.6%. Encapsulation efficiency of SM in nanoparticles was determined using UV spectroscopy after generating calibration plot of SM in methanol ($r^2$=0.9998) at 432 nm (λmax).

Figure 5:
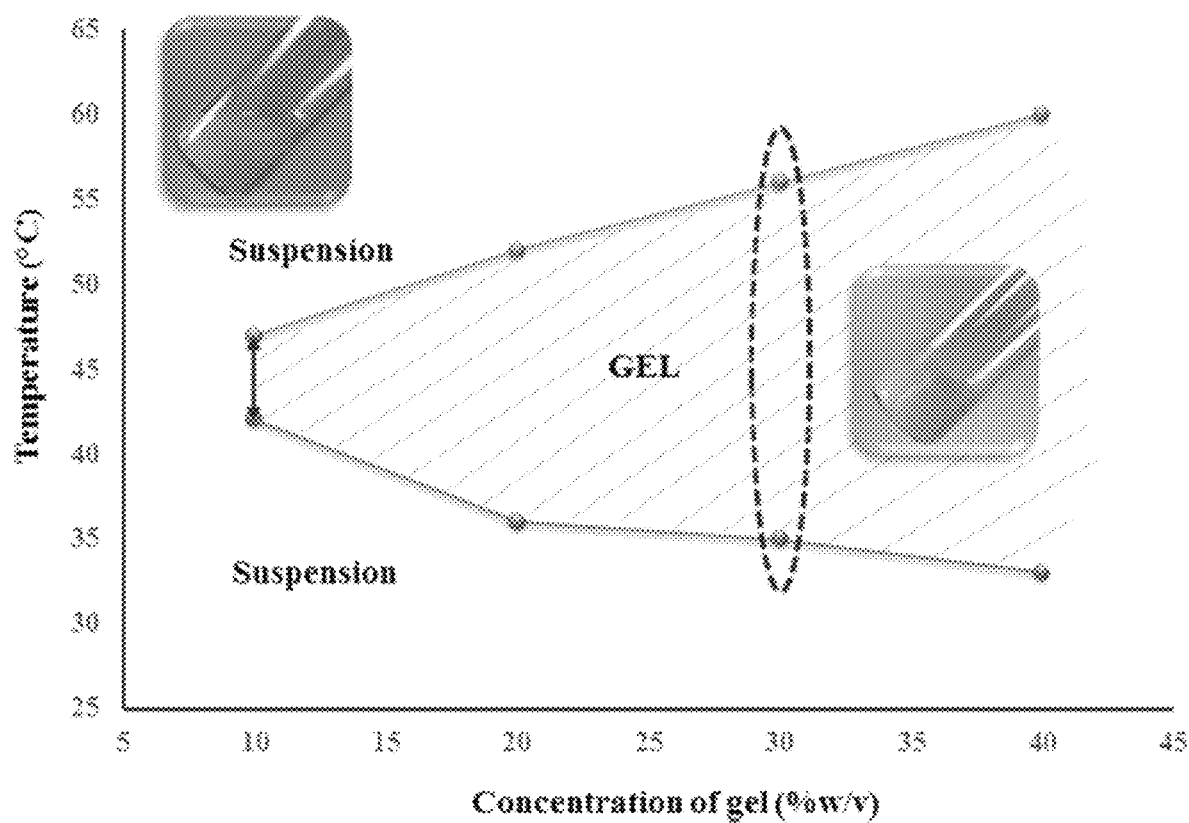
FIG. 5 illustrates phase transition of TR gel from solution to gel with changing temperature at various concentrations of gelling polymer (Phase transition shown by the 30% w/v TR gel depending on change of temperature is shown in inset images).

Preparation of SM-NPs incorporated thermo-reversible gel (SM-NP gel). For the preparation of thermo-reversible gel, Methoxy Poly (ethylene glycol)-b-Polycaprolactone copolymers (AK 036, Polyscitech, USA) was used. Temperature dependent phase transitions of SM-NPs incorporated in AK 036 TR gels with various concentrations was evaluated by visual inspection upon change of temperature from 10° C. to 60° C. (FIG. 5). The 30% w/v TR gel was selected for future studies as its phase transition from liquid to gel took place over 35° C.±2° C. that is physiologically relevant temperature of eye. The phase transition of TR gel at 30% w/v concentration from liquid solution to semisolid gel was observed at around 34° C.

Figure 6:
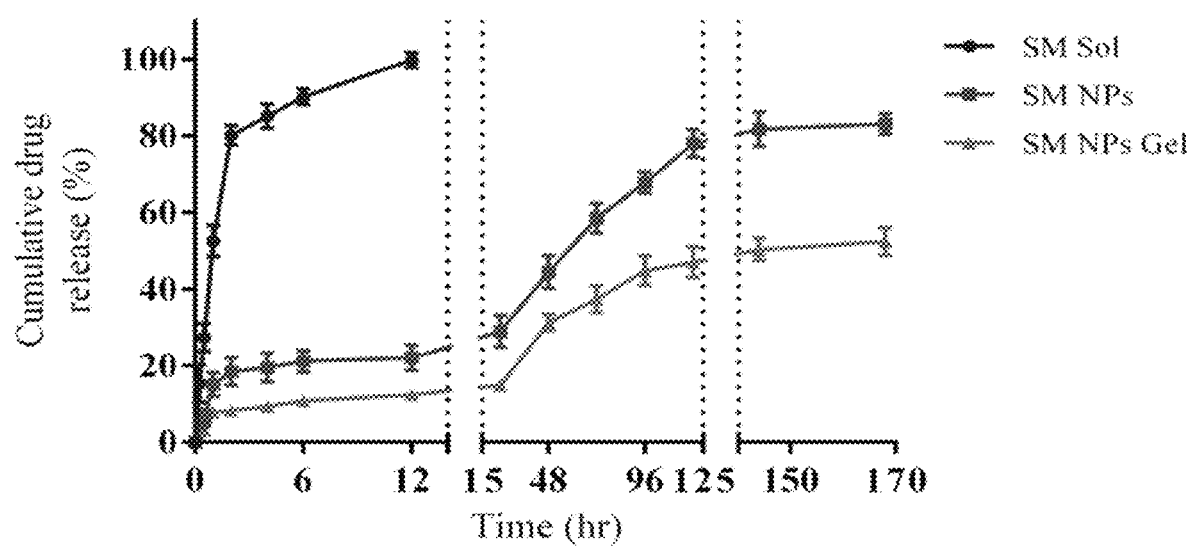
FIG. 6 shows cumulative drug release of SM from SM solution, SM-NPs and SM-NPs thermo-reversible gel up to 7 days at 37° C. in phosphate buffer saline at pH 7.4 (mean±SD, n=3).

In vitro drug release study. The in vitro release study of SM from drug solution, SM-NPs and SM-NPs gel was carried out by dialysis method using PBS (pH 7.4) as release medium at 37° C.±2° C. for a period of 7 days. Further, to maintain sink condition, tween-80 (0.1% v/v) was added to the release medium. Drug was released rapidly into the medium with 80% cumulative release at the end of 3 hr from the drug solution. An initial burst release was observed in the NPs formulations of around 15.1±3.1% in 1 hr which may be due to release of drug from the surface of NP and adhered drug on the surface of NPs. However, SM NPs Gel showed extended release profile with 14.9±1.9% release at the end of first day followed by slow release and showed 52.5±3.6% release content at the end of seven days, while nanoparticles exhibited 29±4.1% and 83.1±2.7% release at end of 1 and 7 days, respectively (FIG. 6).

Cytotoxicity study. The cytotoxicity of the SM drug solution, SM-NPs and SM-NP Gel was studied using the MTT assay in human retinal pigmented epithelium ARPE-19 cell line. Cells were treated in serum free medium with various concentrations (0, 0.001, 0.01, 0.1, 1, 10 and 20 μM) of SM solution, placebo NPs, SM-NPs and SM-NP Gel in triplicates for 24 and 48 h. The resulting cell viability was compared to that of the control, which was established about 100% (FIG. 7). Results indicated that the viability of cells was greater than 90% for SM-NP Gel, SM-NPs and blank nanoparticles at 10 μM and 20 μM concentration tested (p<0.01) whereas, for drug solution viability was found to be 83% and 71% respectively at above concentration, thus indicating cell compatibility of the formulation (FIG. 7).

Figure 8A:
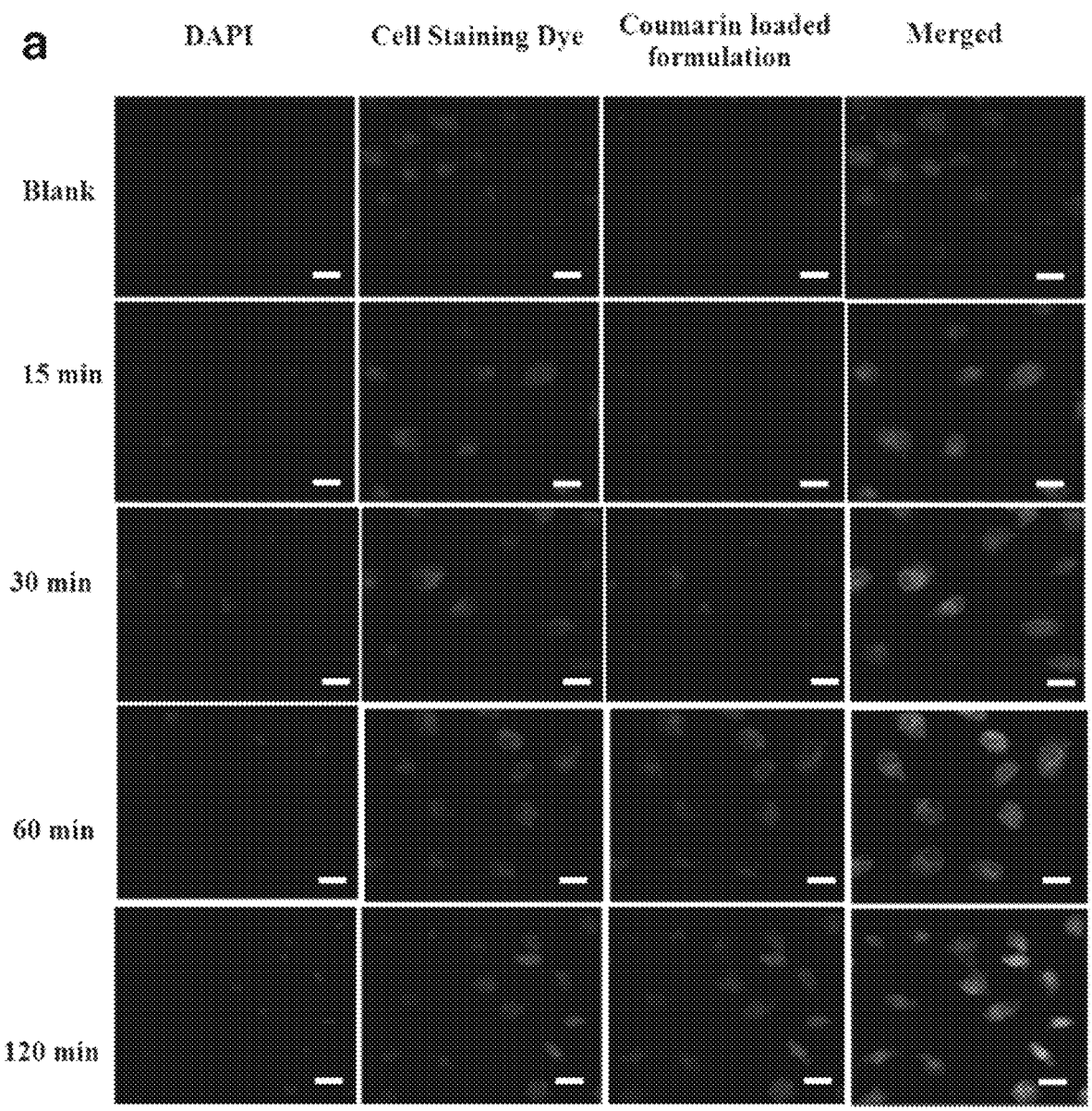
FIGS. 8A and 8B show degrees of cellular uptake of NPs.
Figure 8B:
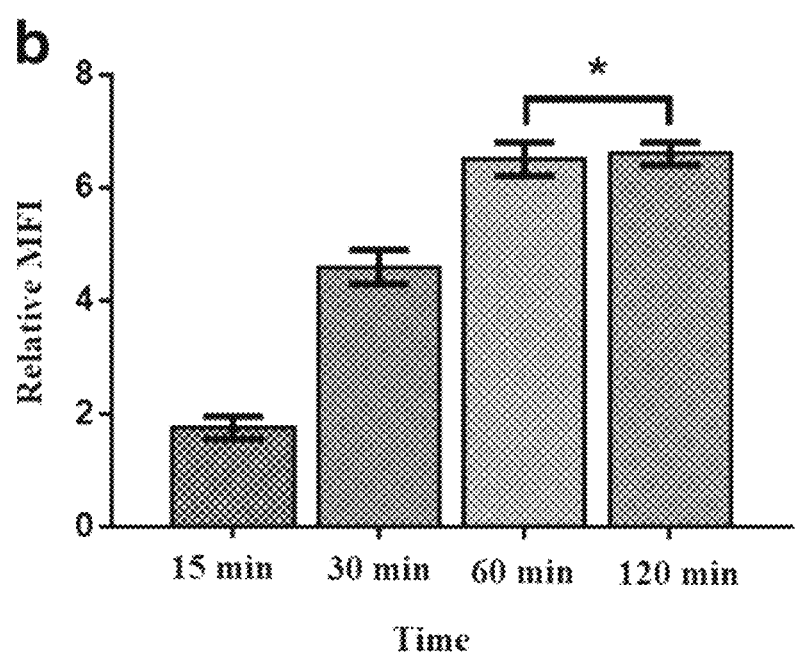

Cellular uptake using confocal microscope Fluorescent (coumarin 6) dye was loaded into to the PLGA NPs to evaluate the uptake of NPs upon incubation in ARPE-19 cells at 37° C. Coumarin-6, a hydrophobic dye was used for this purpose and Coumarin-6 loaded PLGA NPs were prepared using the similar procedure which was used to prepare SM-NPs by loading Coumarin-6 dye instead of SM drug. FIG. 8A shows the uptake of coumarin 6-loaded PLGA NPs into ARPE-19 cells within 2 h of time frame at 37° C. As can be seen the cellular uptake of NPs increased with the time. The relative mean fluorescence intensity was plotted against time (FIG. 8B) increased at 15 min, 30 min and 60 min time points; whereas, the MFI for 60 min and 120 min time points were comparable (p<0.05). The uptake of the NPs by the cells is likely to have occurred via endocytosis. Cells treated with placebo nanoparticles (blank) did not show green fluorescence.

Figure 9A:
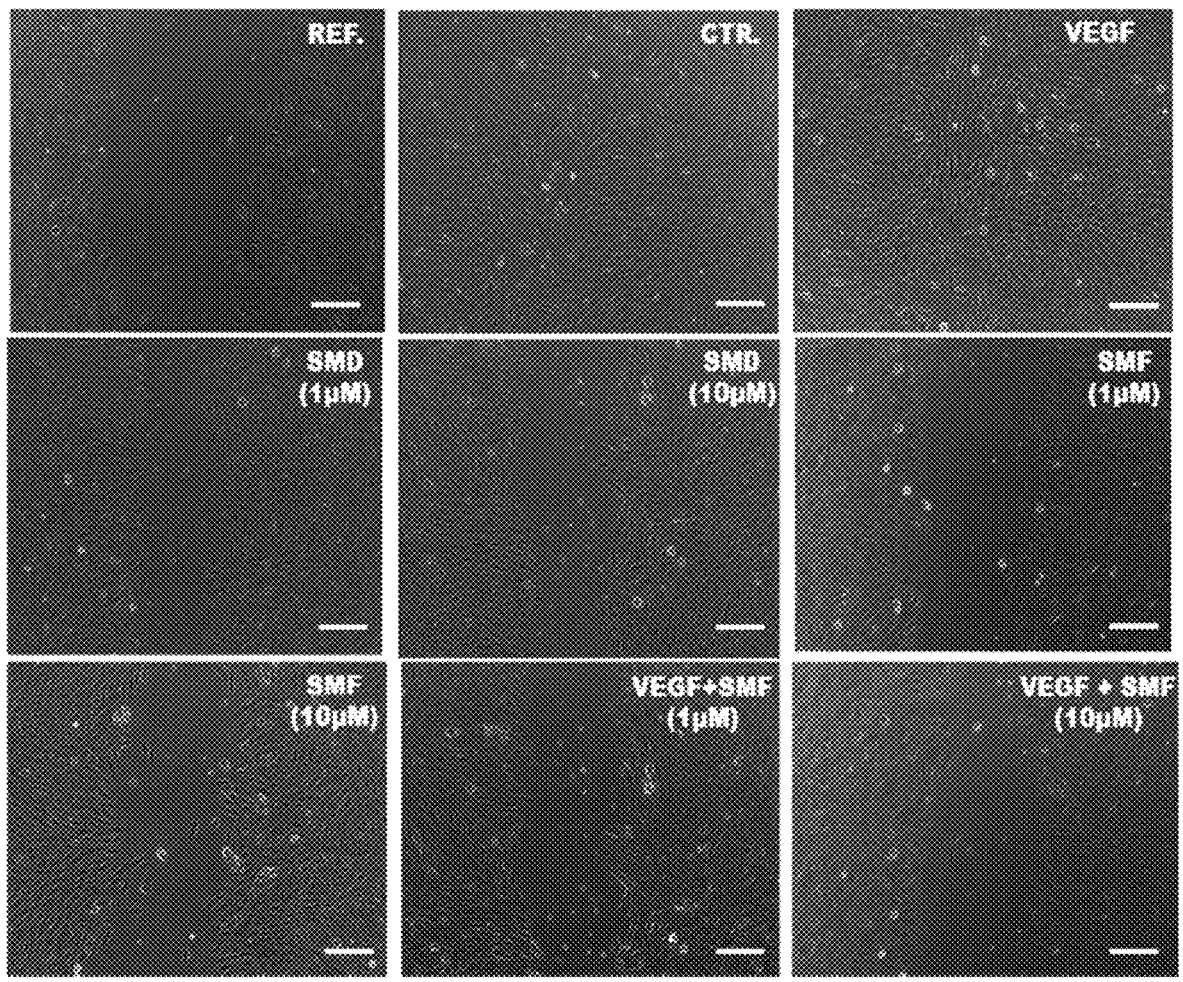
FIGS. 9A and 9B show cell migration upon treatment of NPs.
Figure 9B:
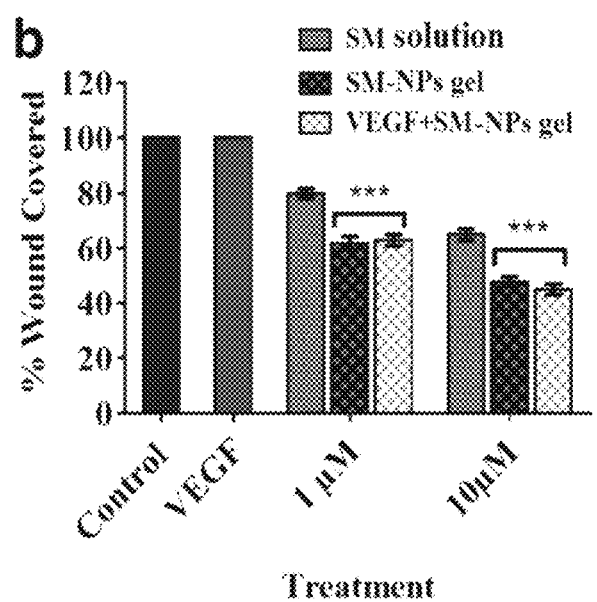

Wound scratch assay. Wound scratch assay was performed for determination of migratory effect on cell in the presence of different formulations. As evident from the FIG. 9A, for control group or the untreated cells, a completed recovery of the wound occurred in comparison to the reference group. With the cells treated with different concentration of SM solution or SM-NP gel or SM-NP gel in the presence of VEGF, concentration-dependent inhibition of cell migration was observed. The percent wound recovered for various treatment groups were plotted as shown in FIG. 9B which shows that the wound recovery was lowest for SM-NPs gel at 10 µM concentration (48±1.9%). Recovery of 80±1.8% was seen at 1 µM concentration for SM solution which was highest among the treated groups. Addition of 100 nM of VEGF165 (rhVEGF; R&D Systems) increased the migration of cells to greatest extent and hence wound recovery, as seen in FIG. 9A. However, co-treatment of SM-NPs gel formulation with VEGF165 hindered the action of VEGF165 as well as inhibited VEGF-induced angiogenic manifestations in ARPE-19 cells and did not significantly improve the cell migration-based wound recovery (63±2% and 45±2.5% for 1 µM and 10 µM concentration, respectively). These results indicate that SM NP gel efficiently and selectively inhibits VEGF-induced angiogenesis in ARPE-19 cells.

Figure 10:
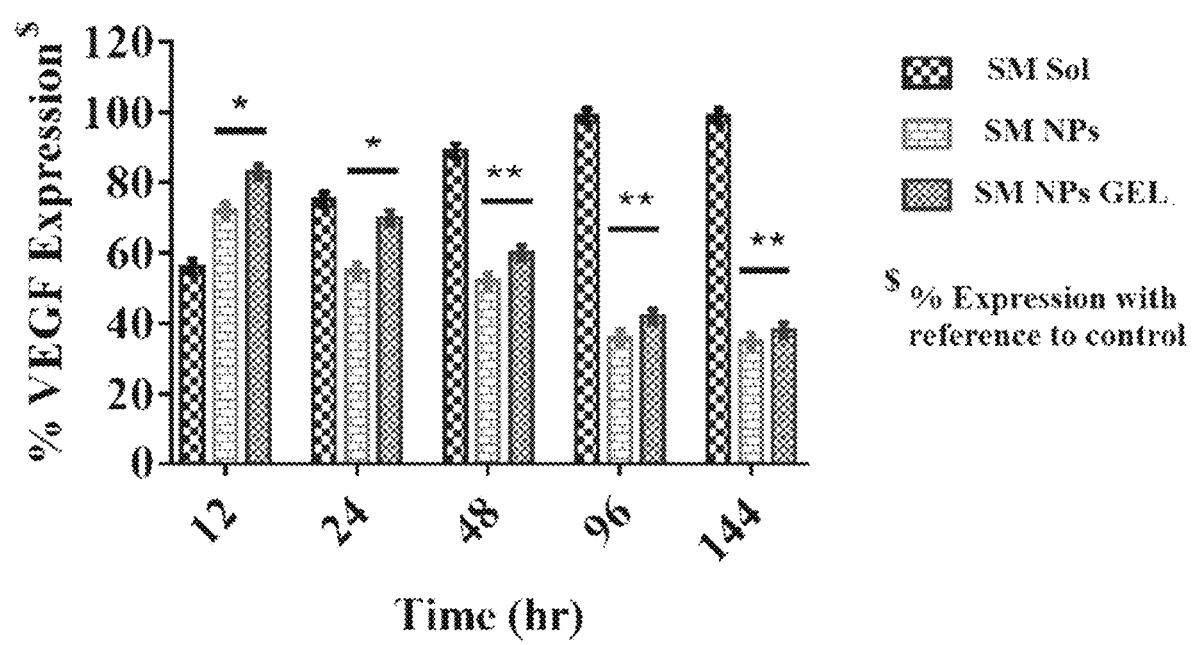
FIG. 10 shows comparison of VEGF expression levels in ARPE-19 cells at different treatment time points for SM solution, SM-NP and SM-NPs gel formulation (*$p<0.05$, **$p<0.01$).

VEGF inhibition using ELISA. The effect of the SM drug solution, SM-NPs and SM NP gel on secretion of VEGF was studied using ARPE-19 cells. Samples were collected after 12, 24 and 48 h of treatment and the amount of VEGF-A was measured using the Human VEGF-A ELISA kit. % VEGF secretion values are illustrated using the control group value as 100% (FIG. 10). VEGF secretion was noticeably reduced by the free SM solution at initial time points of 12 hr compared to the NPs treatment. SM-NPs and SM-NP Gel formulation have similar effects on VEGF-A secretion with p<0.05 and p<0.01. ELISA results showed significantly decreased VEGF protein levels after exposure to SM-NPs (10 µM equivalent of SM) in ARPE-19 at 12, 24, 48, 96, and 144 h in comparison with control cells and cells treated with drug solution.

The treatment alternatives for AMD has gradually shifted to use of anti-VEGF agents or anti-angiogenic agents and investigating their delivery methods to maximizing the therapeutic outcome of therapy of reversing visual loss and improve patient compliance. However, the therapeutic limitations that are associated with their regimen include medical and economic constrain, need of repeated administration and adverse effects such as endophthalmitis. Anti-angiogenic agents inhibit the neovascular proliferation and vascular permeability by selectively inhibiting the binding of VEGF to its receptor as well as the circulating VEGF molecules. Studies have also been carried out to deliver these agents by systemic route; however the associated adverse effects of proteinuria, thromboembolism and hypertension have greatly limited their use. Thus, the need of local delivery of these agents have aroused and culminated in the use of intravitreal route of instillation for these agents. However, this route present multiple challenges to the clinician for determining the drug of choice and selection of dosing schedule. The delivery systems investigated include implants, nano-systems prepared using several non-biodegradable and biodegradable polymers, nano-devices with innovative design etc. with few of the extended release implants that were approved by FDA. However, no such clinically viable alternative available for anti-VEGF agents. Of the biodegradable systems, use of nanoparticles for delivery of anti-VEGF agents for indications such as anti-cancer has been widely investigated; however not much evidence for use in AMD is found. Thus, the purpose of this study was to solve the unmet need during the usage of AMD by designing biocompatible and biodegradable NPs system that improves bioavailability with sustained release property. PLGA being biocompatible and biodegradable, PLGA NPs system can serve as a viable alternative for intravitreal injection of anti-VEGF agents for delivery drug at target site with prolonged release profile. In this study, PLGA nanoparticles incorporating SM were prepared using emulsion solvent evaporation method (FIG. 1) and evaluated for their in vitro performance. As a delivery system to increase the longevity in the physiological environment, the prepared nanoparticles were incorporated in thermo-reversible gel.

As a first step of evaluating the delivery system, formulation compatibility behaviour was investigated. Incompatibility among the polymer and drug can be determined from the shifts in the transition temperature of individual components in DSC and generation of additional peaks in infrared spectra. Further, on successful entrapment of a drug in the polymeric matrix, crystalline peaks of the drug get diminished. DSC and FTIR were carried out to confirm the above theories. The results indicated encapsulation of the drug in nanoparticles with the disappearance of the characteristic crystalline peak of the drug at 202° C. and the comparative similarity of the spectra between blank nanoparticles and sunitinib malate nanoparticles. The characteristic peaks of drug in FTIR at 3322 $cm^{-1}$, 2979 $cm^{-1}$ and 1669 $cm^{-1}$ were also absent in the formulation thus indicating encapsulation of drug in the polymer and drug and polymer are compatible with each other (FIG. 2 and FIG. 3). These results are in agreement with previously published data. Size and charge of the nanoparticles are important physical parameters that determine their fate. The combined effect of size of the nanoparticles was in nano-range (164.5±5.8 nm) (FIGS. 4A-4B) and a high negative zeta potential (−18.27±3.6 mV) prevents aggregation among the nanoparticles and stabilizes against electrostatic interaction forces and also prevents interaction with serum components and protein adsorption. Such interactions lead to the formulation being uptaken by tissue macrophages and subsequent degradation by metabolizing enzymes. TEM images confirmed that the nanoparticles were spherical in shape and were not in aggregated. The incorporation of nanoparticle in the gel formulation was effective in providing sustained release characteristic. The polycaprolactone blocks of polyvivo AK36 imparts longevity in vivo due to slow degradation. The SM-NPs were suspended in 30% w/v of TR gel as its phase transition from liquid to gel took place over physiologically relevant temperatures. From the study of temperature-dependent phase change of various concentrations of TR gel, it was found that as the concentration of TR gel was increased from 10% to 40%, a broader range of temperature was observed in which gelling of solution was attained and stayed in gel phase from liquid (solution) phase. The 20% TR gel also showed phase change from liquid to gel in physiological temperature range. However, 30% concentration was selected as a final formulation because it can sustain the release of drug to the greater extend when compared to 20% w/v of TR gel (data not shown) as well as has a broader temperature range in which it stays as gel phase (FIG. 5). The concentration of TR gel more than 30% w/v showed higher viscosity when in solution phase, presented syringeability issues and was not selected as it does not allow easy intravitreal injection. Formation of nanoparticles entangles the drug molecule in their matrices and thus entraps them. Once entrapped, the release is governed by surface erosion of the matrix and such release can further be controlled by loading the nanoparticles in gelled matrix. Thus, the use of biocompatible gel can be favorable in achieving the sustained release of drug for improving therapeutic outcomes. Presence of free drug form or inefficient entrapment leads to lower entrapment and may also be not useful in controlling the release profile.

Figures 7A, 7B:
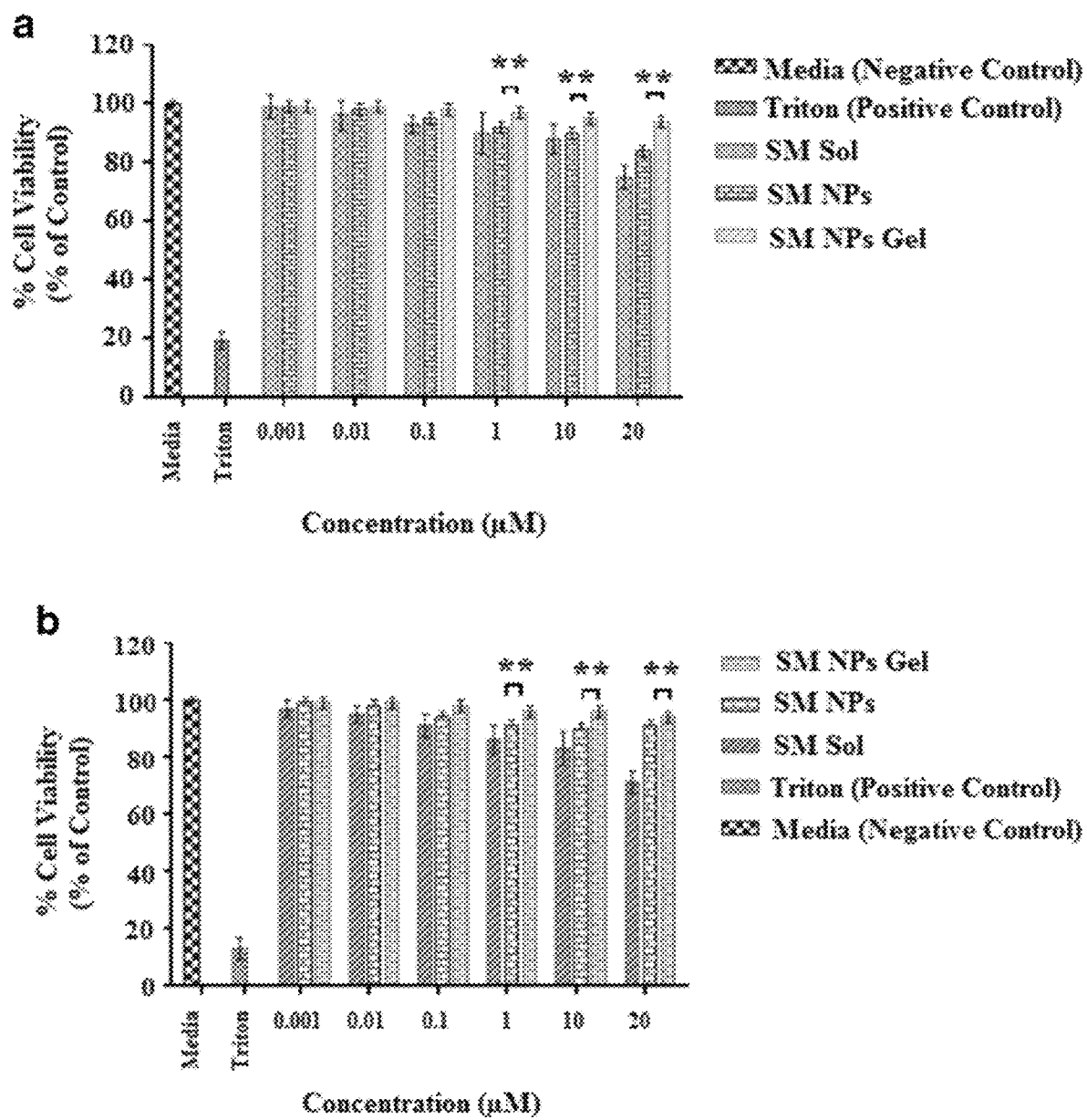
FIGS. 7A and 7B show cell viability plots of ARPE-19 cells after treatment of SM drug solution, SM-NPs, and SM-NPs gel at (FIG. 7A) 24 h and (FIG. 7B) 48 h (mean±SD, n=3; **$p<0.01$).

In vitro release behavior of formulation is important in correlating with the in vivo behavior of the formulations. Unlike other body parts, pH at eye is neutral and hence release study was performed at pH 7.4 and supplemented with 0.1% (v/v) of Tween 80 solution. The use of Tween 80 was to favor sink condition and enhance solubilization potential of the medium. As evident from FIG. 6, the SM solution presented no resistance to solubilization or release into the media and showed 80%±2.5% cumulative release within an hour. This indicates that solution dosage form can rapidly release a pool of drug at the site, out of which only a fraction can be absorbed or available for therapeutic effect and most of the drug would get metabolized. For SM-NPs and SM-NP gel formulation, there was a significant ($p<0.05$) difference in the release behavior with gel form exhibiting slower release profile compared to NPs formulation. This can be due to the additional diffusional barrier present by incorporating NPs in gel matrix. From the relative comparison of the release profiles of NPs gel against NPs, it was deduced that NPs gel release rate was in range of 1.4 to 2.2-fold lower compared to NPs release rate at different time points over the entire release period. For release kinetics, SM drug solution followed first order drug release with $R^2$ of 0.9683; however, SM-NPs followed Higuchi model with $R^2$ of 0.9845. This indicates that the release mechanism is determined by the diffusion of drug through the polymeric gel matrix and is time dependent. The MTT results indicate that the nanoparticulate formulation as well its gelled formulation both were less cytotoxic than the solution form of drug indicating safety of the formulations (FIGS. 7A-7B). It is evident from the viability results that there is dose-dependent cytotoxic potential of plain drug solution at a higher concentration of 20 µM with 25-30% of viability lost at 24 h and 48 h respectively. However, for SM-NPs and SM-NP gel formulations, the cell viability remained greater than 90% indicating the formulations were not exhibiting a toxic effect on ARPE-19 cells. At 1, 10, and 20 µM concentration of SM NPs there was non-significant ($p<0.01$) difference in % cell viability at the end of 48 h time point. This lower cytotoxic potential of the formulation is an important consideration that was exhibited due to the use of PLGA/PCL as matrix-forming agents and is approved polymer by US Food and Drug Administration (FDA) and hence most widely used biocompatible polymer in drug delivery. Furthermore, the sustained release of drug from the NP formulations reinstates equilibrium between the amount of drug and number of cells exposed to the released quantity of formulation at a particular point of time thus maximizing the uptake and minimizing the undue drug overload to the cells. The time-dependent increase in the fluorescence of the nanoparticles indicates that the mechanism of uptake can be mediated by interaction with receptor and as the ARPE-19 cells express VEGF receptor, endocytosis can be the most rational mechanism for the cellular uptake. The relative MFIs at 15, 30, and 60 min were 1.8±0.2%, 4.6±0.3%, and 6.5±0.3%, respectively, which indicated that the cumulative uptake of the nanoparticles and drug load in the cells increased as a function of time. Furthermore, the relative MFI at 120 min was 6.6±0.2% which was non-significant ($p<0.05$) with respect to the uptake at 60-min duration and indicated that no further uptake can have taken place or there was a saturation of the receptor-mediated uptake (FIG. 8). Angiogenesis involves a number of synchronized events of the cells that include their proliferation, migration, and morphogenesis. The angiogenic potential of the cells can be studied and demonstrated by cell-based migration assay. A quantitative evaluation of inhibition of cell migration substantiates the effectiveness of NP formulation and can be extrapolated to in vivo behavior as well. The formulation with the highest efficacy has the lowest recovery in cell migration and vice versa. Taking into consideration the viability of cells according to FIG. 7 and 10 µM equivalent concentration of SM-NPs was selected as highest screened. Wound scratch assay showed (FIG. 9) a significant effect ($p<0.001$) of SM-NP treatment with VEGF on ARPE-19 cell migration compared with SM-NPs. Further, compared with the drug solution, the wound recovery observed was 20% lower for SM-NPs suggesting that the formulation exhibited anti-proliferative effect. As already mentioned, there was concentration-dependent cell proliferation inhibition observed for the cells treated with nanoparticle formulation. To confirm that the inhibition of proliferation was due to the inhibition of VEGF activity, ARPE-19 cells were treated with exogenous VEGF along with NP formulation treatment and wound recovery was monitored. The inhibition of cell migration in these co-treatment regimens confirmed the effectiveness of the drug entrapped in the nanoparticle formulation. Finally, to confirm the expression levels of VEGF levels in the ARPE-19 cells, ELISA test was performed on the various treatment groups. Although from the three-treatment group involving SM solution, SM-NPs, and SM-NP gel, the drug solution exhibited strongest inhibition (56±3%) of VEGF levels at initial time point of 12 h compared with the other two (72±3% and 83±4% for SM-NPs and SM-NP gel respectively) (FIG. 10); it showed weak control at subsequent time points. This can be due to the initial high level of free drug available to the cells due to solution form, and that can also be correlated to the release profile of the formulation. However, in the case of nanoparticle formulation and its gel, there was an initial low level of VEGF control which at later time points became stronger as the drug release from the matrix occurred over longer duration. At the end of 48 h, the expression levels for the nanoparticles and gel formulation were almost 50% and 60%, respectively, whereas those in solution-treated cells displayed no inhibition (90% VEGF expression levels). Herein, a point to note is the higher inhibitory effect of nanoparticle formulation compared with its gelled incorporated form having significant differences at 12 h and 24 h, whereas the two groups showed non-significant differences at 48, 96, and 144 h ($p<0.01$). This is due to slower release of drug from the gel matrix compared with its free nanoparticle form. However, taking into consideration that the NP-based gel formulation can sustain the release of drug from the formulation for even longer period, these expression levels can sustain at subsequent time points leading to effective control over in VEGF expressed in the treatment group. Overall, the drug-loaded NPs showed promising results and its application for treating AMD.

Example 2. Nanoparticulate Ophthalmic Drug Delivery Systems Using Polymeric Thermo-Reversible Materials In this study, the model drugs triamcinolone acetonide (TA), Loteprednol Etabonate (LE) and Sunitinib Malate (SM) were encapsulated by PLA-PEG-PLGA nanoparticles (NPs) and further incorporated into a PLGA-PEG-PLGA thermo-reversible gel. PLGA NPs loaded with each drug individually were prepared by nano-precipitation method and were characterized to check their size, entrapment efficiency, in vitro drug release profile and in vitro cytotoxicity. The TA-loaded NPs showed an average particle size of 208.00±1.00 nm and poly-dispersity index (PDI) of 0.12±0.03 using DLS technique while for LE-loaded NPs, particle size was found to be 168.60±23.18 nm and PDI was 0.08±0.003 and for SM-loaded NPs it was 164.5±5.8 nm and 0.09±0.002 respectively. TEM images demonstrated nanoparticles of uniform size and were in concurrence with the DLS results and were spherical with smooth surface. The encapsulation efficiency of TA, LE and SM loaded PLGA NPs were found to be 26.3%, 82.6% and 72%, respectively. The prepared PLGA NPs were further incorporated into a PLGA-PEG-PLGA thermo-reversible gel. For that 20% (w/v) thermo-reversible gel was prepared using cold method. In vitro release analysis demonstrated that free TA from TA solution was completely released within 24 hours; whereas 94% of TA was released from PLGA-PEG-PLGA thermo-reversible gel after 7 days. SM loaded nanoparticles PLGA-PEG-PLGA thermo-reversible gel also showed extended release profile with 15% release at the end of first day followed by slow release till 52% at the end of seven days, while nanoparticles without incorporating in gel exhibited 29% and 83% release at end of 1 and 7 days. Whereas, for drug solution more than 80% release was seen in 3 hours. Similarly, in vitro release results of LE loaded NPs gel also demonstrated sustained release profile at the end of 7 days in vitro release study. Cytotoxicity test (MTT assay) in human retinal pigmented epithelium (ARPE-19) cell line indicated that the viability of cells was greater than 90% for gel loaded, as such and blank nanoparticles at 10 μM and 20 μM concentration tested whereas, for drug solution viability was found to be 72% and 54%, respectively, at above concentrations, thus indicating cell compatibility of the formulation. In vivo studies conducted in mice shown positive results in reduction of macular degeneration.

Example 3. Thermo-Reversible Gel Formulation Containing Sunitinib Loaded PLGA Nanoparticles for Ocular Delivery Anti-vascular endothelial growth factor (anti-VEGF) agents have been widely used to treat several eye diseases such as proliferative diabetic retinopathy, age-related macular degeneration and retinal vein occlusion. However, their oral/systemic administration is associated with severe side effects such as hypertension and renal disorders, thus limiting their therapeutic potential for ocular diseases. Thus, there is a need to design approach that will maximize the local concentration of drug at target site and at the same time minimize the systemic exposure. Sunitinib, one such agent used herein, is a multiple receptor tyrosine kinase inhibitor that selectively inhibits VEGF receptor, platelet-derived growth factor receptors, stem cell growth factor receptor and colony stimulating factor receptor. Inhibition of these multiple receptors associated with choroidal neovascularization may provide a more complete blockade of the neo-angiogenesis process compared to currently available monotherapy agents (such as aflibercept, bevacizumab or ranibizumab), without need for co-administered intravitreal agents. Herein, to maximize the tissue exposure in retinal fluid and to minimize systemic bioavailability, PLGA encapsulated nanoparticles of sunitinib were formulated that imparted extended release and to further increase the residence time in the vitreal fluid they were incorporated in thermo-reversible gel. The formulation was evaluated for physicochemical properties and in vitro performance. The optimized formulation has defined characteristic for intravitreal injection.

Particle size of nanoparticles was found to be 164.5±5.8 nm. Zeta potential was found to be −5.68±1.8 mV. Entrapment efficiency was found 72.0%±3.5%. Percent drug loading was found to be around 9%. DSC and FTIR results indicated encapsulation of the drug in nanoparticles with disappearance of characteristic drug peaks in both the cases. TEM images demonstrated nanoparticles of uniform size and were in concurrence with the DLS results and were spherical with smooth surface. Release study result for the gel incorporated nanoparticles showed extended release profile with 15% release at the end of first day followed by slow release till 52% at the end of seven days, while nanoparticles exhibited 29% and 83% release at end of 1 and 7 days. Whereas, for drug solution more than 80% release was seen in 3 hours. Cytotoxicity test (MTT assay) in human retinal pigmented epithelium (ARPE-19) cell line indicated that the viability of cells was greater than 90% for gel loaded, as such and blank nanoparticles at 10 μM and 20 μM concentration tested whereas, for drug solution viability was found to be 83% and 71% respectively at above concentration, thus indicating cell compatibility of the formulation.

Sunitinib-loaded nanoparticles were developed, characterized and tested in vitro in cells of human ocular epithelial cell line demonstrating its usefulness in ocular delivery to treat neovascularization associated diseases. The gelled formulation exhibited extended release characteristic and non-cytotoxicity to the cell. This formulation is clinically useful compared to the oral formulations that exhibit meagre efficacy in the diseased condition. The intravitreal instillation of the prepared thermo-gelling nanoparticles can be an alternative to the current treatment strategies.

What is claimed is:

1. A nanogel drug composition, comprising:
   a nanogel, wherein the nanogel comprises a thermal reversible nanogel, and wherein the thermal reversible nanogel comprises a methoxy poly (ethylene glycol)-b-polycaprolactone copolymer; and
   at least one nanoparticle comprising a poly (lactic-co-glycolic acid) polymer and sunitinib or a pharmaceutically acceptable salt thereof.

2. The nanogel drug composition of claim 1, wherein the nanoparticle has a diameter from about 100 nm to about 250 nm.

3. The nanogel drug composition of claim 1, wherein the nanoparticle has a diameter from about 150 nm to about 175 nm.

4. A pharmaceutical composition comprising: the nanogel drug composition of claim 1; and a pharmaceutical acceptable carrier.

5. A method of treating age-related macular degeneration in a subject in need thereof, comprising: administering to the subject a therapeutically effective amount of a nanoparticle comprising a poly (lactic-co-glycolic acid) polymer and sunitinib or a pharmaceutically acceptable salt thereof, wherein the nanoparticle is in a nanogel drug composition comprising a nanogel, wherein the nanogel comprises a thermal reversible nanogel, and wherein the thermal reversible nanogel comprises a methoxy poly (ethylene glycol)-b-polycaprolactone copolymer.

6. The method of claim 5, wherein the nanoparticle has a diameter from about 100 nm to about 250 nm.

7. The method of claim 5, wherein the nanoparticle has a diameter from about 150 nm to about 175 nm.

8. The method of claim 5, wherein the subject is a human.

9. The method of claim 5, wherein the nanogel drug composition is administered to the subject through intravitreal route.

10. The method of claim 5, wherein the nanogel drug composition is administered once a month.

11. The nanogel drug composition of claim 1, wherein the nanoparticle has a zeta potential ranging from about −10 mV to about −80 mV.

12. The nanogel drug composition of claim 11, wherein the nanoparticle has a zeta potential about −18 mV.

13. The method of claim 5, wherein the nanoparticle has a zeta potential ranging from about −10 mV to about −80 mV.

14. The method of claim 13, wherein the nanoparticle has a zeta potential about −18 mV.

* * * * *